(12) United States Patent
Kimura et al.

(10) Patent No.: US 8,822,674 B2
(45) Date of Patent: Sep. 2, 2014

(54) CRYSTAL FORM OF 4-ISOPROPYLPHENYL GLUCITOL COMPOUND AND PROCESS FOR PRODUCTION THEREOF

(75) Inventors: Yoshihiro Kimura, Toshima-ku (JP); Koreaki Imura, Toshima-ku (JP); Naoto Osaki, Toshima-ku (JP); Ayumi Matsushima, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 23 days.

(21) Appl. No.: 13/816,647

(22) PCT Filed: Aug. 19, 2011

(86) PCT No.: PCT/JP2011/068736
§ 371 (c)(1),
(2), (4) Date: Feb. 12, 2013

(87) PCT Pub. No.: WO2012/023598
PCT Pub. Date: Feb. 23, 2012

(65) Prior Publication Data
US 2013/0144050 A1    Jun. 6, 2013

(30) Foreign Application Priority Data

Aug. 20, 2010 (JP) .................................. 2010-184854
Aug. 26, 2010 (JP) .................................. 2010-189739

(51) Int. Cl.
*C07H 7/04* (2006.01)
(52) U.S. Cl.
USPC .......................................... 536/53; 536/55.3
(58) Field of Classification Search
CPC ........................................................ C07H 7/04
USPC .................................................. 536/53, 55.3
See application file for complete search history.

(56) References Cited

U.S. PATENT DOCUMENTS

| 8,466,113 B2 * | 6/2013 | Kakinuma et al. ............... 514/23 |
| 2010/0022460 A1 | 1/2010 | Kakinuma et al. |
| 2011/0306759 A1 | 12/2011 | Kakinuma et al. |

FOREIGN PATENT DOCUMENTS

| EP | 1544208 | 6/2005 |
| JP | 2009107997 | 5/2009 |
| JP | 2009537509 | 10/2009 |
| WO | 2004014932 | 2/2004 |
| WO | 2007136116 | 11/2007 |
| WO | 2010095768 | 8/2010 |

OTHER PUBLICATIONS

International Preliminary Report on Patentability for PCT/JP2011/068736 dated Mar. 19, 2013, with Written Opinion.

* cited by examiner

*Primary Examiner* — Traviss C McIntosh, III
(74) *Attorney, Agent, or Firm* — Sughrue Mion, PLLC

(57) ABSTRACT

A highly stable crystal of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol, and a process for producing the crystal are provided. Specifically, an ethanolate having the following physical properties, and a plurality of other crystal forms transformed from the ethanolate are provided:

(a) Having peaks at 2θ=5.9 degrees, 17.1 degrees, 17.6 degrees and 21.5 degrees in X-ray powder diffraction (Cu—Kα);
(b) Showing characteristic absorption bands at 3538 $cm^{-1}$, 3357 $cm^{-1}$, 2964 $cm^{-1}$, 1673 $cm^{-1}$, 1634 $cm^{-1}$ and 1505 $cm^{-1}$ in an infrared absorption spectrum; and
(c) Having a melting point in a vicinity of 111° C.

6 Claims, 11 Drawing Sheets

CRYSTAL FORM OF 4-ISOPROPYLPHENYL GLUCITOL COMPOUND AND PROCESS FOR PRODUCTION THEREOF

CROSS REFERENCE TO RELATED APPLICATIONS

This application is a National Stage of International Application No. PCT/JP2011/068736 filed Aug. 19, 2011, claiming priority based on Japanese Patent Application Nos. 2010-184854 filed Aug. 20, 2010 and 2010-189739 filed Aug. 26, 2010, the contents of all of which are incorporated herein by reference in their entirety.

TECHNICAL FIELD

This invention relates to a crystal form of 4-isopropylphenyl glucitol, which is useful as an active ingredient of a therapeutic agent for diabetes, and a process for producing the crystal form.

BACKGROUND ART

Blood glucose levels are used as a biomarker for metabolic syndrome, and people are diagnosed as having diabetes if their fasting blood glucose levels exceed 126 mg/dL. Moreover, even if fasting blood glucose levels fall within a normal range, some people have 2-hour postprandial blood glucose levels as high as 140 to 200 mg/dL and are diagnosed as having impaired glucose tolerance (or postprandial hyperglycemia). Recent epidemiological studies have reported that impaired glucose tolerance increases the risk of cardiovascular disorders (see Non-Patent Documents 1 and 2). Further, it has been reported that exercise therapy and/or medication not only suppresses the development of type II diabetes from impaired glucose tolerance, but also significantly suppresses the onset of hypertension (see Non-Patent Document 3).

In view of the foregoing, suppression of postprandial hyperglycemia is of importance in suppressing the onset of diabetes and/or metabolic syndrome, and there has accordingly been an increasing demand for drugs used to control postprandial hyperglycemia.

As agents for improving postprandial hyperglycemia, α-glucosidase inhibitors have been conventionally used widely, which inhibit sugar hydrolases and thereby delay sugar absorption from the small intestine. In addition to these agents, there have been developed other agents with a new mechanism of action for improving postprandial hyperglycemia.

On the mammalian small intestinal epithelium, sodium-dependent glucose transporter 1 (SGLT1) is expressed at a high frequency. It is known that SGLT1 serves depending upon sodium and plays a role in active transport of glucose or galactose in the small intestine. Based on these findings, pyrazole derivatives have been reported, which inhibit SGLT1 activity to thereby suppress glucose absorption from a meal and can be used for prevention or treatment of postprandial hyperglycemia (see Patent Documents 1 to 6). On the other hand, sodium-dependent glucose transporter 2 (SGLT2) is expressed at a high frequency in the kidney, and glucose once filtered by the glomeruli is reabsorbed via SGLT2 (see Non-Patent Document 4). Moreover, it has been reported that upon inhibition of SGLT2 activity, sugar excretion into urine is facilitated to induce a hypoglycemic action (see Non-Patent Document 5). SGLT2 inhibitors are characterized in that they have an excellent hypoglycemic action to lower casual blood glucose levels, but their action to control postprandial hyperglycemia is low, unlike SGLT1 inhibitors. Further, there is a report of C-phenyl glucitol derivatives which inhibit not only SGLT1 activity but also SGLT2 activity at the same time (see Patent Document 7).

On the other hand, in the case of drugs required to be administered continuously, including agents for improving postprandial hyperglycemia, it is important to have a wide margin of safety between the therapeutic dose and the toxic or side effect dose. Particularly in the case of drugs prone to remain in the body, it is difficult to control their dosage required for treatment, so that an excessive drug effect will be developed as a result of summing residual drugs remaining in the body, thus leading to unexpected toxicity and side effects. For example, it is known that cationic drugs whose molecule has a hydrophilic group (e.g., a tertiary amine) and a hydrophobic group (e.g., an aromatic ring) bind to phospholipids through hydrophobic bonding and are taken up by lysosomes and hence accumulated in all organs in the body. As typical examples, chloroquine is shown to cause retinopathy, while perhexyline gives rise to a problem of neuropathy because it induces changes in the lung and cerebellum (see Non-Patent Document 6).

Thus, drugs are desired to be rapidly excreted from the body after developing their efficacy. In particular, agents for improving postprandial hyperglycemia that must be administered continuously are desired to be free from the problem of accumulation in the body.

On the other hand, ease of handling on an industrial scale, and physical properties including excellent storage stability of products are demanded of pharmaceuticals.

CITATION LIST

Patent Documents

Patent Document 1: International Publication WO2002/098893 pamphlet
Patent Document 2: International Publication WO2004/014932 pamphlet
Patent Document 3: International Publication WO2004/018491 pamphlet
Patent Document 4: International Publication WO2004/019958 pamphlet
Patent Document 5: International Publication WO2005/121161 pamphlet
Patent Document 6: International Publication WO2004/050122 pamphlet
Patent Document 7: International Publication WO2007/136116 pamphlet

Non-Patent Documents

Non-Patent Document 1: Pan X R, et al. Diabetes Care, Vol. 20, p. 537, 1997
Non-Patent Document 2: M Tominaga, et al. Diabetes Care, Vol. 22, p. 920, 1999
Non-Patent Document 3: J.-L. Chiasson, et al. Lancent, Vol. 359, p. 2072, 2002
Non-Patent Document 4: E. M. Wright, Am. J. Physiol. Renal. Physiol., Vol. 280, p. F10, 2001
Non-Patent Document 5: G. Toggenburger, et al. Biochim. Biophys. Acta, Vol. 688, p. 557, 1982

Non-Patent Document 6: Folia Pharmacol. Jpn. Vol. 113, p. 19, 1999

SUMMARY OF INVENTION

Technical Problem

An object of the present invention is to provide a crystal of a novel compound which exhibits SGLT1 inhibiting action with a wide margin of safety between a therapeutic dose and a toxic or adverse effect dose, and which is excellent in the aforementioned physical properties.

Solution to Problem

The present inventors have conducted diligent studies in an attempt to attain the above-mentioned object. As a result, they have found that (1S)-1,5-anhydro-1-[5-(4-{(E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol (may hereinafter be referred to as compound (A)) exhibits SGLT1 inhibiting action with a wide margin of safety between a therapeutic dose and a toxic or adverse effect dose; that its ethanolate can provide a crystal of the novel compound showing the aforementioned excellent physical properties; and that the ethanolate enables the crystal to be easily changed into other crystal forms. These findings have led them to accomplish the present invention.

An aspect of the present invention is a crystal of an ethanolate of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol having the following physical properties (a) to (c):
(a) Having peaks at 2θ=5.9 degrees, 17.1 degrees, 17.6 degrees and 21.5 degrees in X-ray powder diffraction (Cu—Kα);
(b) Showing characteristic absorption bands at 3538 cm$^{-1}$, 3357 cm$^{-1}$, 2964 cm$^{-1}$, 1673 cm$^{-1}$, 1634 cm$^{-1}$ and 1505 cm$^{-1}$ in an infrared absorption spectrum; and
(c) Having a melting point in the vicinity of 111° C.

Another aspect of the present invention is a process for producing a crystal having the physical properties (a) to (c) mentioned below, comprising: dissolving (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol in ethanol or a mixture of ethanol and an organic solvent miscible with ethanol; then effecting crystallization at 0 to 80° C.; and drying the resulting crystal at 50° C. or lower.
(a) Having peaks at 2θ=5.9 degrees, 17.1 degrees, 17.6 degrees and 21.5 degrees in X-ray powder diffraction (Cu—Kα);
(b) Showing characteristic absorption bands at 3538 cm$^{-1}$, 3357 cm$^{-1}$, 2964 cm$^{-1}$, 1673 cm$^{-1}$, 1634 cm$^{-1}$ and 1505 cm$^{-1}$ in an infrared absorption spectrum; and
(c) Having a melting point in the vicinity of 111° C.

Another aspect of the present invention is a crystal (A-form crystal) of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol having the following physical properties (a) to (b):
(a) Having peaks at 2θ=6.1 degrees, 13.7 degrees, 18.0 degrees and 18.7 degrees in X-ray powder diffraction (Cu—Kα); and
(b) Having a melting point in the vicinity of 110° C.

Another aspect of the present invention is a process for producing a crystal (A-form crystal) having the physical properties (a) to (b) mentioned below, comprising: suspending an ethanolate of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol in water or a phosphate buffer solution; and then drying the resulting crystal at 35° C. or lower.
(a) Having peaks at 2θ=6.1 degrees, 13.7 degrees, 18.0 degrees and 18.7 degrees in X-ray powder diffraction (Cu—Kα); and
(b) Having a melting point in the vicinity of 110° C.

Another aspect of the present invention is a crystal (B-form crystal) of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol having the following physical properties (a) to (b):
(a) Having peaks at 2θ=6.4 degrees, 10.9 degrees, 16.9 degrees and 18.1 degrees in X-ray powder diffraction (Cu—Kα); and
(b) Having a melting point in the vicinity of 115° C.

Another aspect of the present invention is a process for producing a crystal (B-form crystal) having the physical properties (a) to (b) mentioned below, comprising: suspending an ethanolate of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol in a mixture of isopropyl ether and an organic solvent (excluding ethanol) miscible with isopropyl ether, or a mixture of hexane or heptane and an organic solvent (excluding ethanol) miscible with hexane or heptane; and then drying the resulting crystal at room temperature to 100° C.:
(a) Having peaks at 2θ=6.4 degrees, 10.9 degrees, 16.9 degrees and 18.1 degrees in X-ray powder diffraction (Cu—Kα); and
(b) Having a melting point in the vicinity of 115° C.

Another aspect of the present invention is a crystal (C-form crystal) of (1S)-1,5-anhydro-1-[5-(4-{(1E)-4-[(1-{[2-(dim-ethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol having the following physical properties (a) to (b):
(a) Having peaks at 2θ=10.7 degrees, 17.9 degrees and 19.7 degrees in X-ray powder diffraction (Cu—Kα); and
(b) Having a melting point in the vicinity of 127° C.

Another aspect of the present invention is a process for producing a crystal (C-form crystal) having the physical properties (a) to (b) mentioned below, comprising: increasing the temperature of a crystal (A-form crystal) of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol to a temperature ranging from room temperature to 150° C. under reduced pressure conditions; then suspending the crystal in a solvent mixture of hexane and ethyl acetate; and then drying the resulting crystal at 35° C. or lower:
(a) Having peaks at 2θ=10.7 degrees, 17.9 degrees, and 19.7 degrees in X-ray powder diffraction (Cu—Kα); and
(b) Having a melting point in the vicinity of 127° C.

Another aspect of the present invention is a crystal (a crystal of a dihydrate) of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol having the following physical properties (a) to (b):

(a) Having peaks at 2θ=17.2 degrees, 17.8 degrees and 20.9 degrees in X-ray powder diffraction (Cu—Kα); and
(b) Having a melting point in the vicinity of 121° C.

Another aspect of the present invention is a process for producing a crystal (a crystal of a dihydrate) having the physical properties (a) to (b) mentioned below, comprising: suspending an ethanolate of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol in a mixture of isopropyl ether and methanol; and then drying the resulting crystal at room temperature:

(a) Having peaks at 2θ=17.2 degrees, 17.8 degrees and 20.9 degrees in X-ray powder diffraction (Cu—Kα); and
(b) Having a melting point in the vicinity of 121° C.

Advantageous Effects of Invention

An ethanolate of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol is a crystal form stable at a temperature in the vicinity of room temperature, and is excellent in storage stability. Moreover, this compound can be purified to high purity by a simple method, and is thus excellent for industrial production. Furthermore, the ethanolate can be easily changed into other crystal forms in accordance with a purpose to be attained.

DESCRIPTION OF EMBODIMENTS

Modes for carrying out the present invention will be concretely described below.

The compound of the present invention, (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol, (may hereinafter be referred to as compound (A)) has the following chemical structural formula:

[Formula 1]

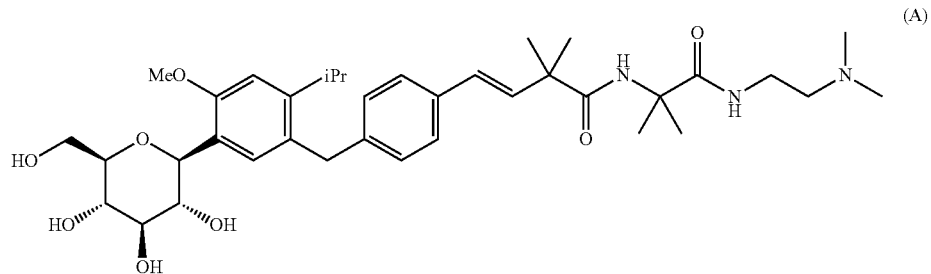

(A)

An ethanolate of the compound (A) (may hereinafter be referred to as the "crystal of the present invention") is obtained reproducibly as a single crystal having constant quality, can be stably supplied as a crystal of a bulk drug for use in the production of pharmaceuticals, and has excellent storage stability. Moreover, the crystal of the present invention is suspended in water or an organic solvent (excluding ethanol), and thereby can be easily changed into other crystal forms. Differences among these crystal forms are discerned, particularly, by X-ray powder diffraction and differential thermal analysis/thermogravimetric analysis curves. The term "crystal of the present invention" means concepts including a mixture of an ethanolate and an anhydride crystal, and a mixed crystal containing an ethanolate and an anhydride crystal.

The ethanolate of the compound (A) has the following physical properties (a) to (c):

(a) Having peaks at 2θ=5.9 degrees, 17.1 degrees, 17.6 degrees and 21.5 degrees in X-ray powder diffraction (Cu—Kα);
(b) Showing characteristic absorption bands at 3538 cm$^{-1}$, 3357 cm$^{-1}$, 2964 cm$^{-1}$, 1673 cm$^{-1}$, 1634 cm$^{-1}$ and 1505 cm$^{-1}$ in an infrared absorption spectrum; and
(c) Having a melting point in the vicinity of 111° C., preferably of 108° C. to 114° C.

Figure 1:
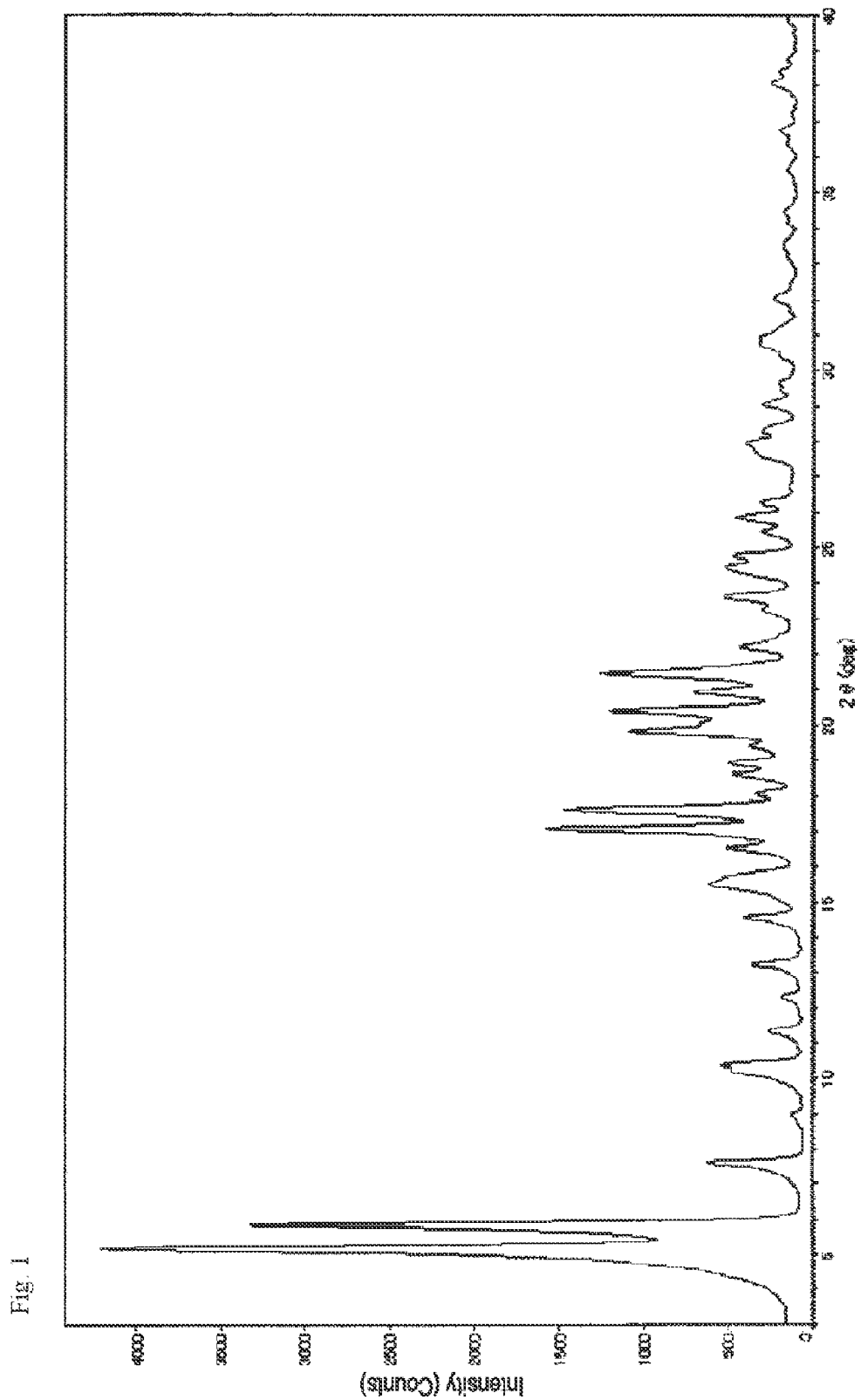
FIG. 1 shows the X-ray powder diffraction pattern of the ethanolate.
Figure 2:
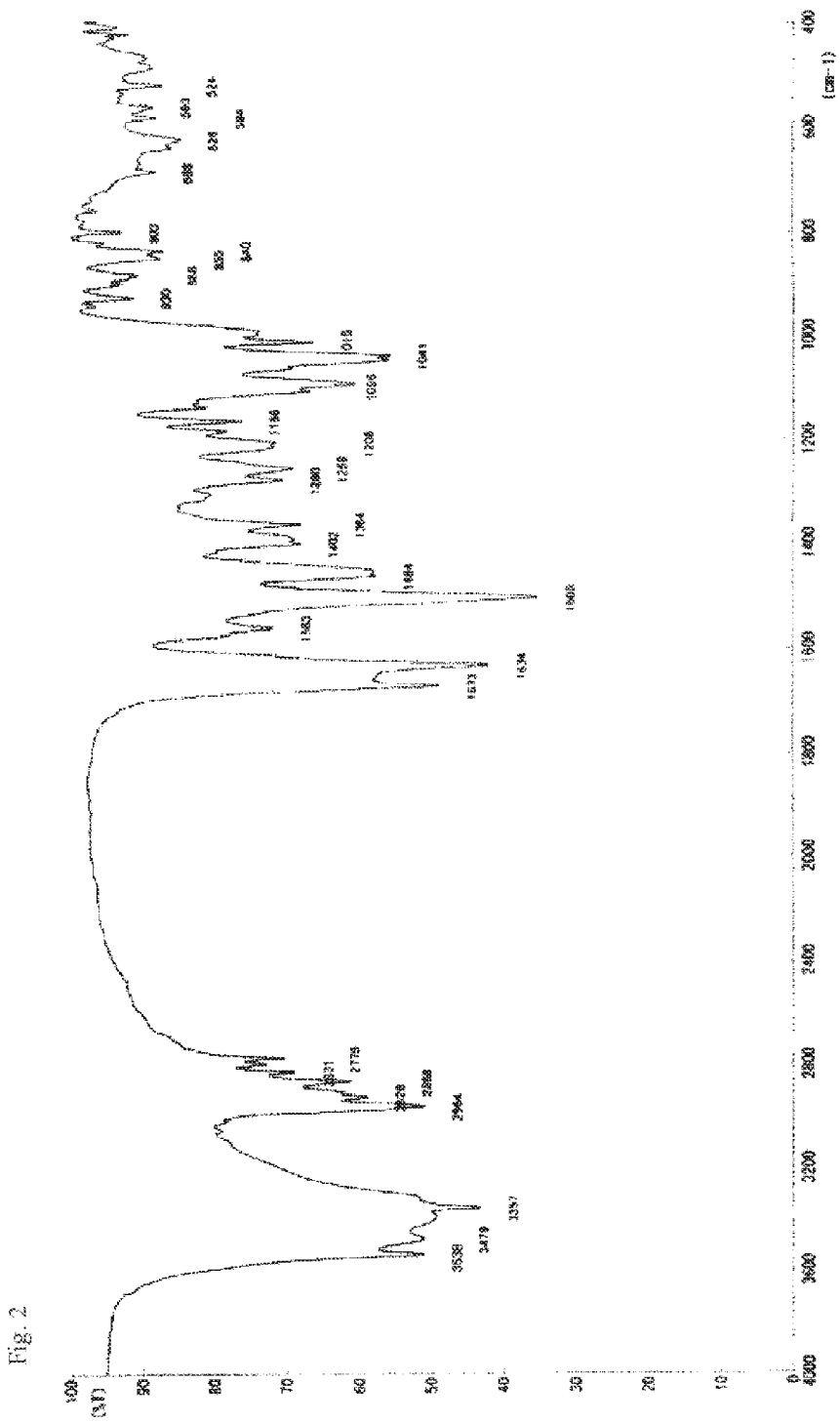
FIG. 2 shows the infrared absorption spectrum (KBr method) of the ethanolate.
Figure 3:
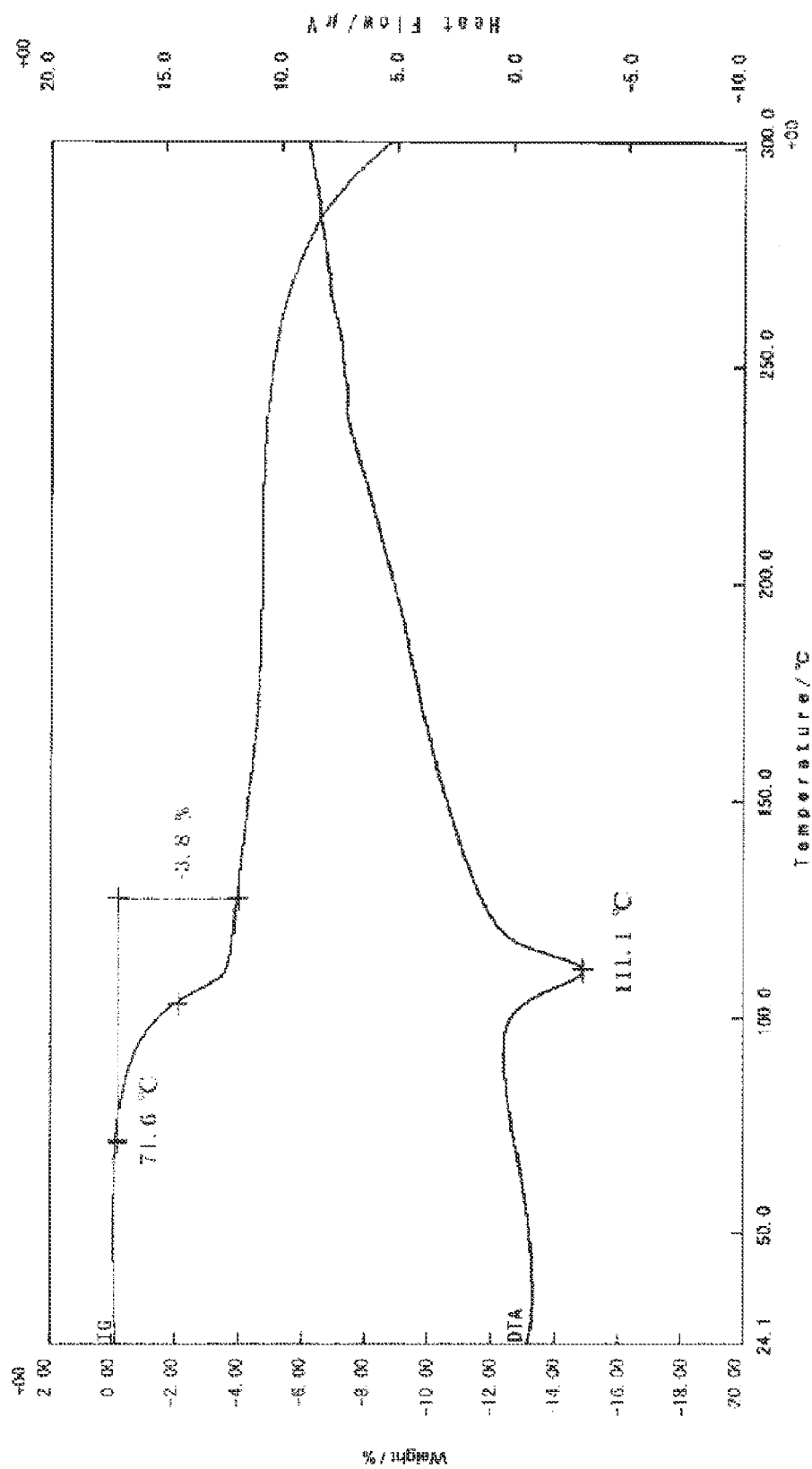
FIG. 3 shows the differential thermal analysis/thermogravimetric analysis curves of the ethanolate.

The X-ray powder diffraction pattern of the ethanolate of the compound (A) is as shown in FIG. 1, the infrared absorption spectrum (KBr method) of the ethanolate is as shown in FIG. 2, and the differential thermal analysis/thermogravimetric analysis curves of the ethanolate are as shown in FIG. 3.

The ethanolate of the compound (A) is obtained by crystallization from a solution having the compound (A) dissolved in ethanol or a mixture of ethanol and an organic solvent miscible with ethanol.

The compound (A) as the raw material before recrystallization is amorphous.

In obtaining the ethanolate by recrystallization from the solution, dissolution of the compound (A) in the solution and crystallization from the solution may be performed by ordinary methods. For example, there is employed a method which comprises dissolving amorphous compound (A), with heating, in a mixture of ethanol and an organic solvent miscible with ethanol, followed by cooling the resulting solution.

Examples of the organic solvent miscible with ethanol are hydrocarbons such as heptane, t-butyl methyl ether, and ethyl acetate.

The concentration at which the compound (A) is dissolved is 0.5 to 70% by mass, preferably 5 to 50% by mass. The term "% by mass" refers to the percent by mass of the ethanolate of the compound (A) in the solution or suspension.

The mixing ratio, in the solvent mixture, between ethanol and the organic solvent miscible with ethanol can be changed as appropriate.

The crystallization of the ethanolate is performed at 0 to 80° C.

The crystal of the ethanolate that has precipitated is separated from the solvent by filtration, centrifugation, etc. of the solution, and is then dried at 50° C. or lower.

The A-form crystal of the compound (A) has the following physical properties (a) to (b):

(a) Having peaks at $2\theta = 6.1$ degrees, 13.7 degrees, 18.0 degrees and 18.7 degrees in X-ray powder diffraction (Cu—K$\alpha$); and (b) Having a melting point in the vicinity of 110° C., preferably of 107° C. to 113° C.

Figure 4:
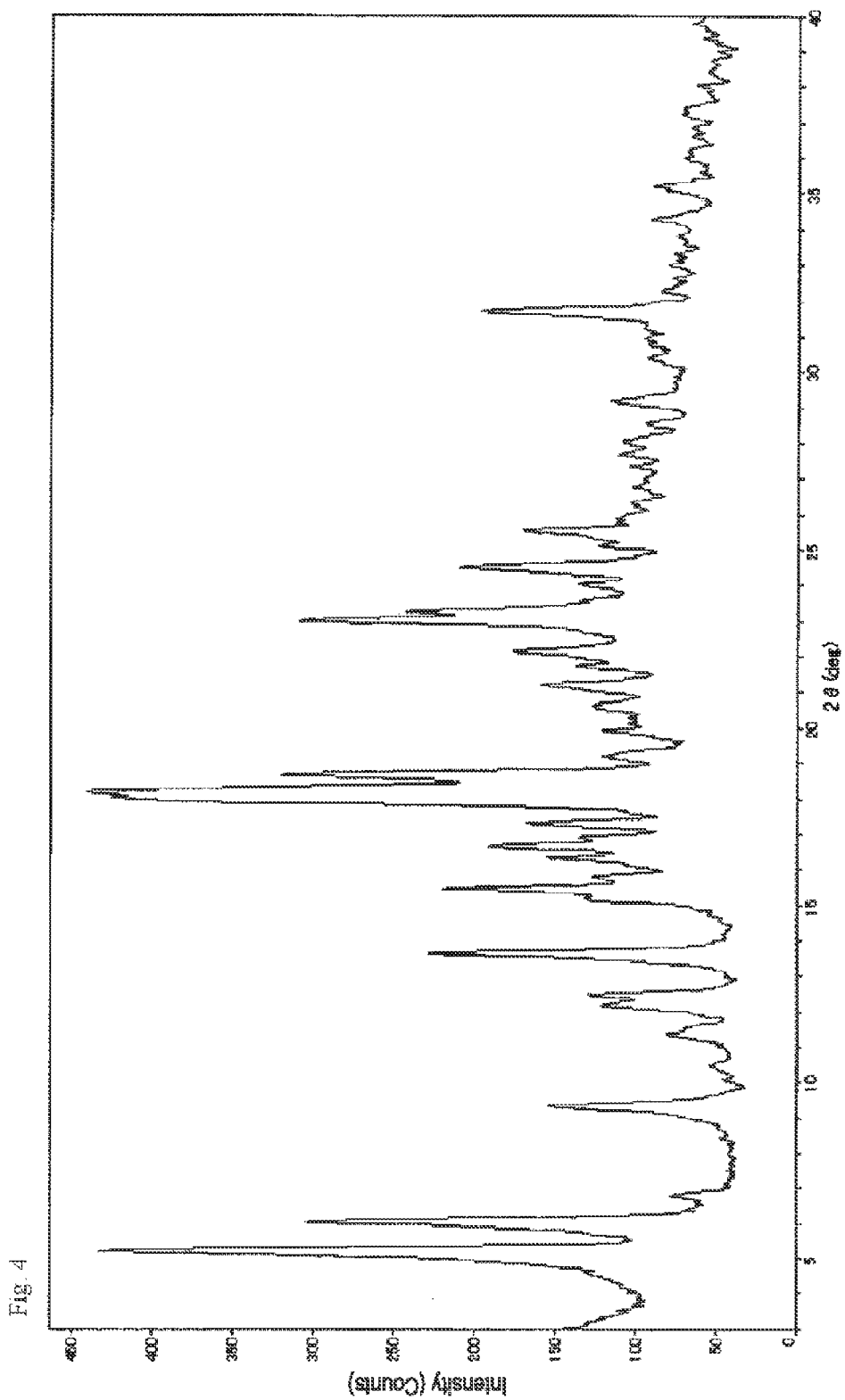
FIG. 4 shows the X-ray powder diffraction pattern of the A-form crystal.
Figure 5:
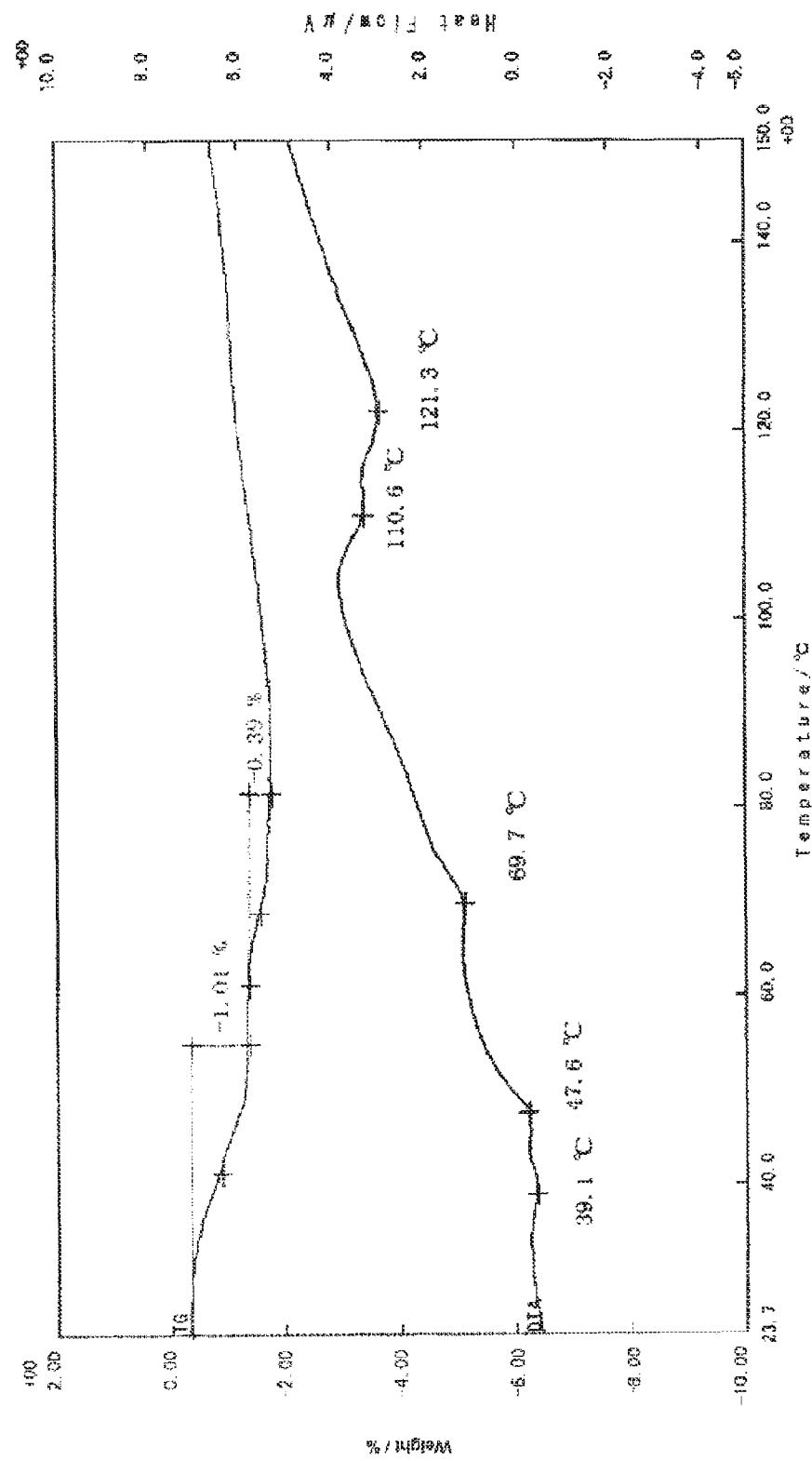
FIG. 5 shows the differential thermal analysis/thermogravimetric analysis curves of the A-form crystal.

The X-ray powder diffraction pattern of the A-form crystal of the compound (A) is as shown in FIG. 4, and the differential thermal analysis/thermogravimetric analysis curves thereof are as shown in FIG. 5.

The A-form crystal of the compound (A) is obtained by suspension of the ethanolate of the compound (A) in water or a phosphate buffer solution.

Examples of the phosphate usable in the phosphate buffer solution are phosphoric acid, sodium dihydrogen phosphate and its hydrate (e.g., dihydrate), disodium hydrogen phosphate and its hydrate (e.g., dodecahydrate), potassium dihydrogen phosphate and its hydrate, and dipotassium hydrogen phosphate and its hydrate.

The concentration at which the ethanolate of the compound (A) is suspended is 0.5 to 30% by mass, preferably 1 to 20% by mass, relative to the suspension.

The suspending temperature is 35° C. or lower, and normally 25° C.

The suspending time is not necessarily set to be constant, depending on the type of the solvent, the temperature, and other conditions. When the suspending temperature is 25° C., the suspending time is 24 hours or more, and normally 24 hours. The conditions for suspending may be those which do not impair the suspended state of the compound (A), and the time for conversion into the A-form crystal can be shortened by raising the temperature. The end point of conversion into the A-form crystal can be confirmed by filtering off some of the crystal from the suspension, and measuring the X-ray powder diffraction pattern of this crystal.

The A-form crystal obtained as above is separated from the solvent, for example, by filtration or centrifugation of the dispersion (suspension), and is then dried at 35° C. or lower, normally at room temperature (25° C.).

No matter which of the above-mentioned methods is adopted, the drying time is not necessarily set to be constant, depending on the drying temperature, the crystal form of the raw material used, the particle size, or other conditions. The end point of the change in the crystal form can be confirmed by taking out some of the dried crystal, and measuring the X-ray powder diffraction pattern of the crystal taken.

The B-form crystal of the compound (A) has the following physical properties (a) to (b):

(a) Having peaks at $2\theta = 6.4$ degrees, 10.9 degrees, 16.9 degrees and 18.1 degrees in X-ray powder diffraction (Cu—K$\alpha$); and (b) Having a melting point in the vicinity of 115° C., preferably of 112° C. to 118° C.

Figure 6:
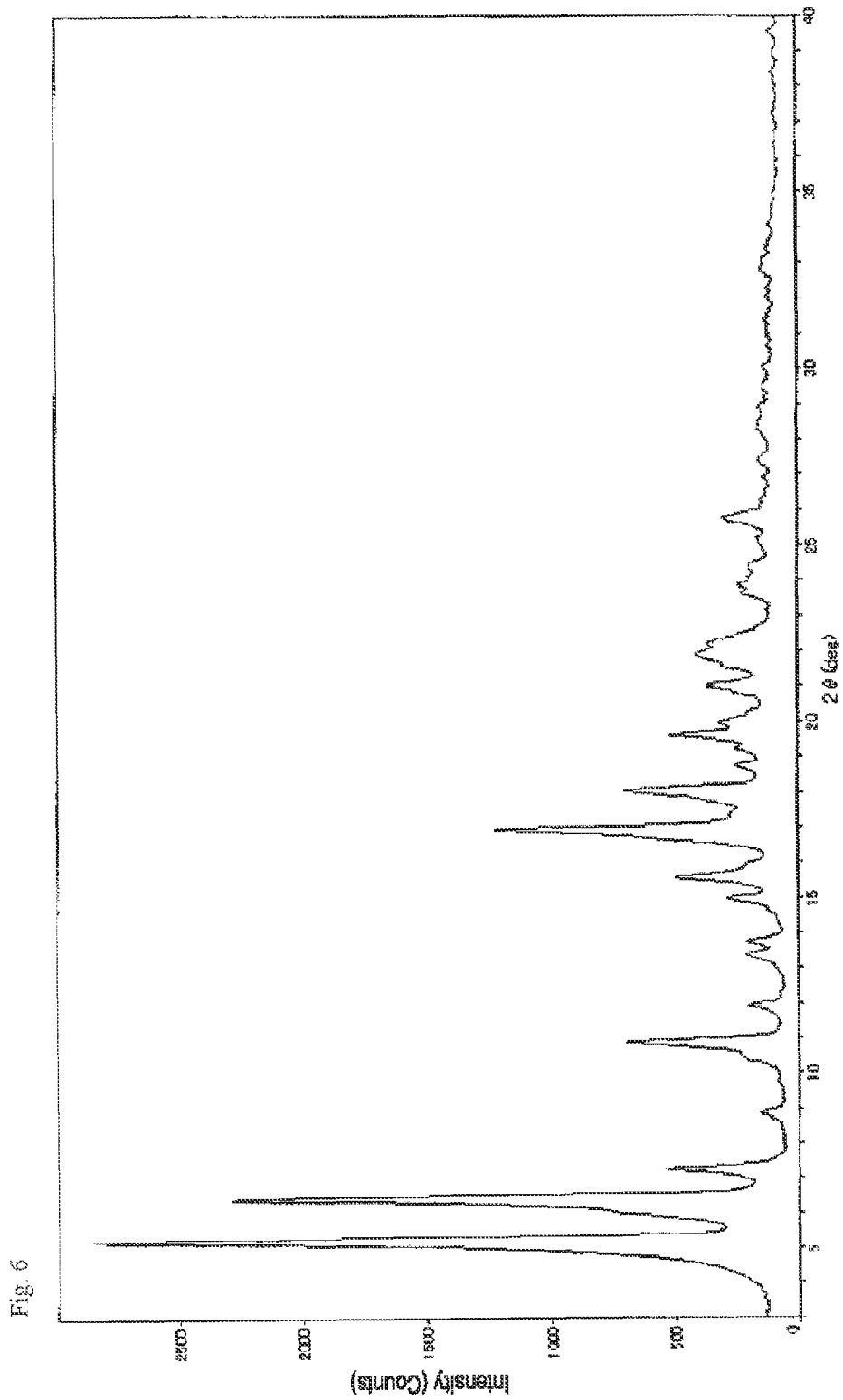
FIG. 6 shows the X-ray powder diffraction pattern of the B-form crystal.
Figure 7:
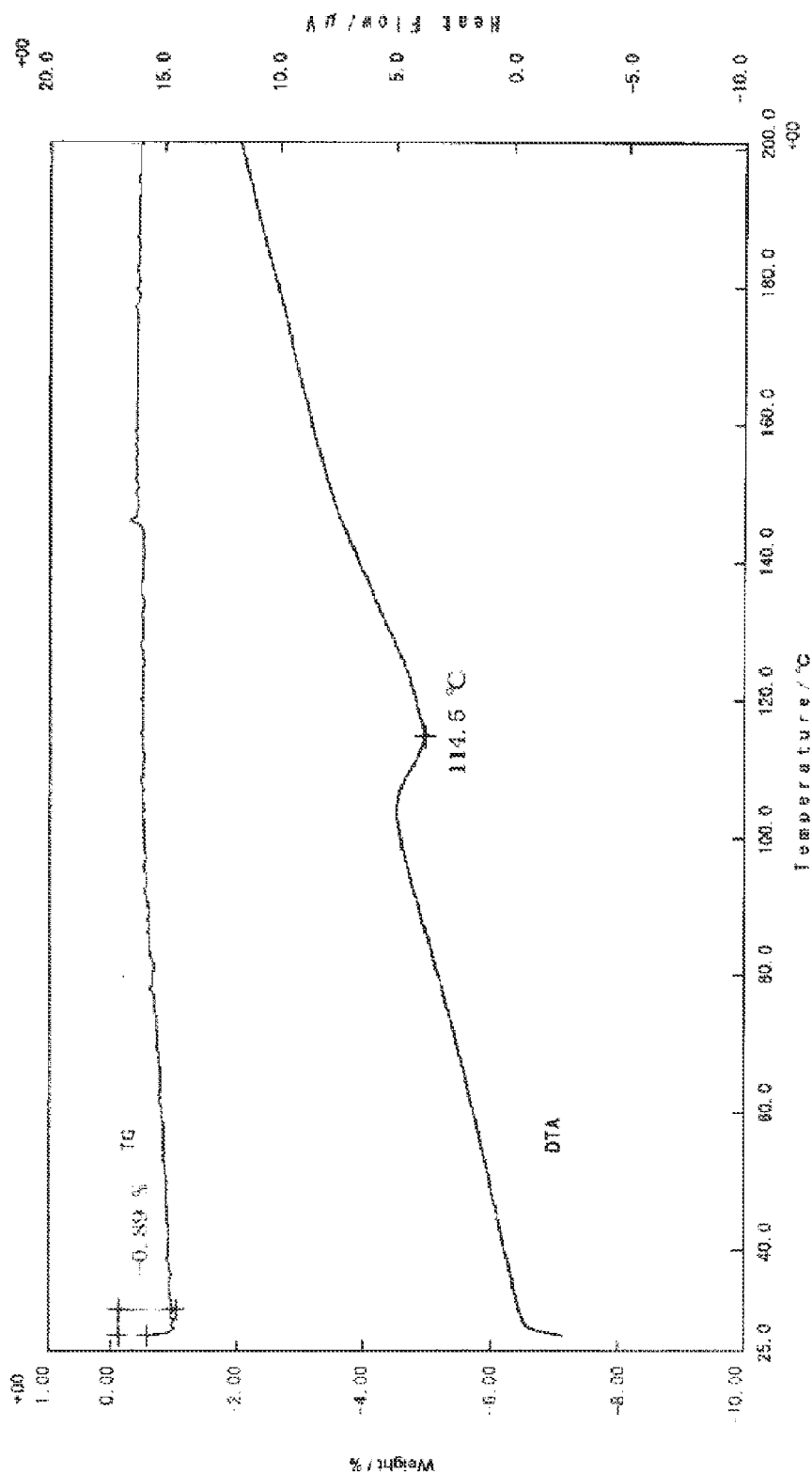
FIG. 7 shows the differential thermal analysis/thermogravimetric analysis curves of the B-form crystal.
Figure 8:
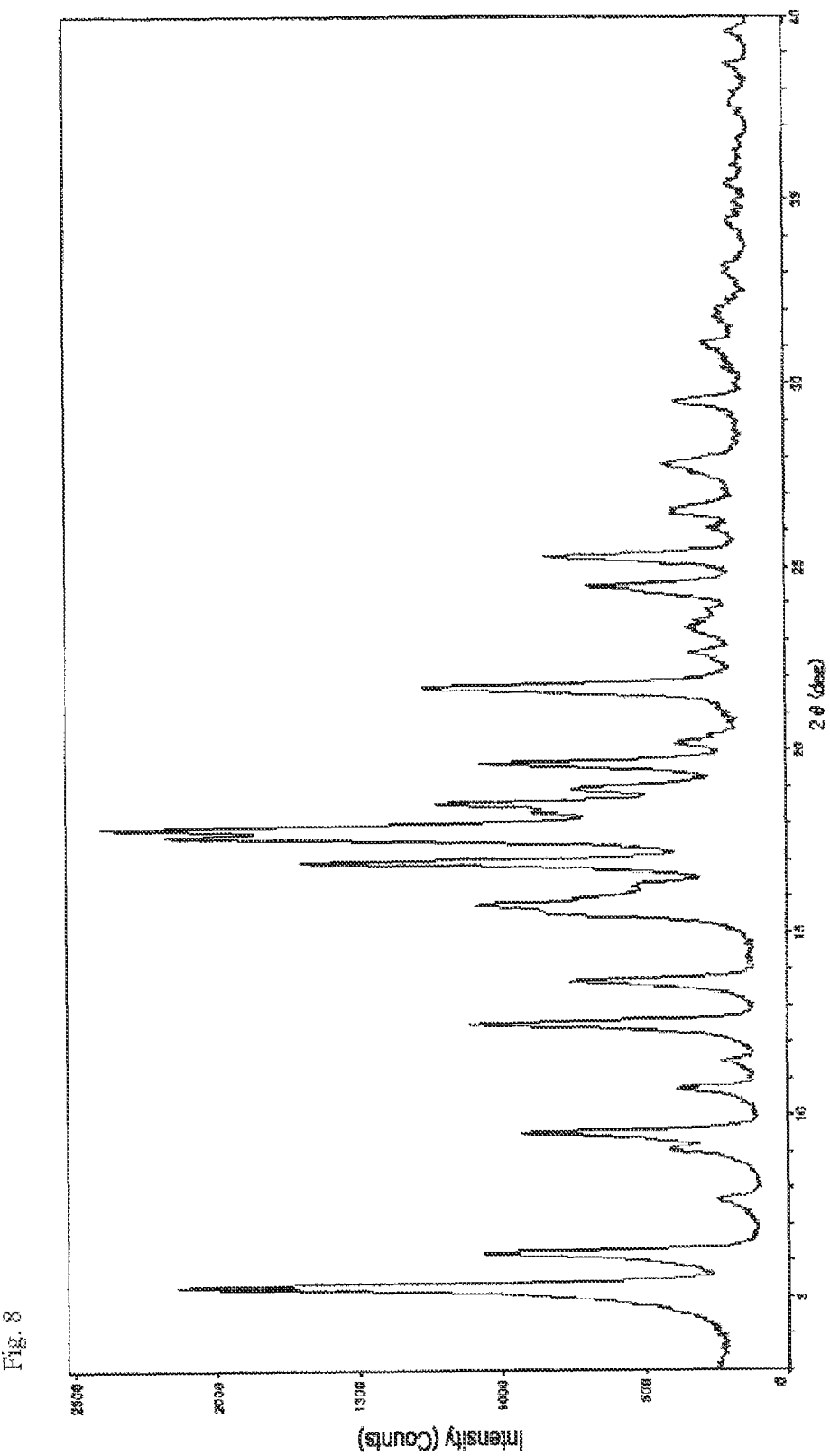
FIG. 8 shows the X-ray powder diffraction pattern of the C-form crystal.
Figure 9:
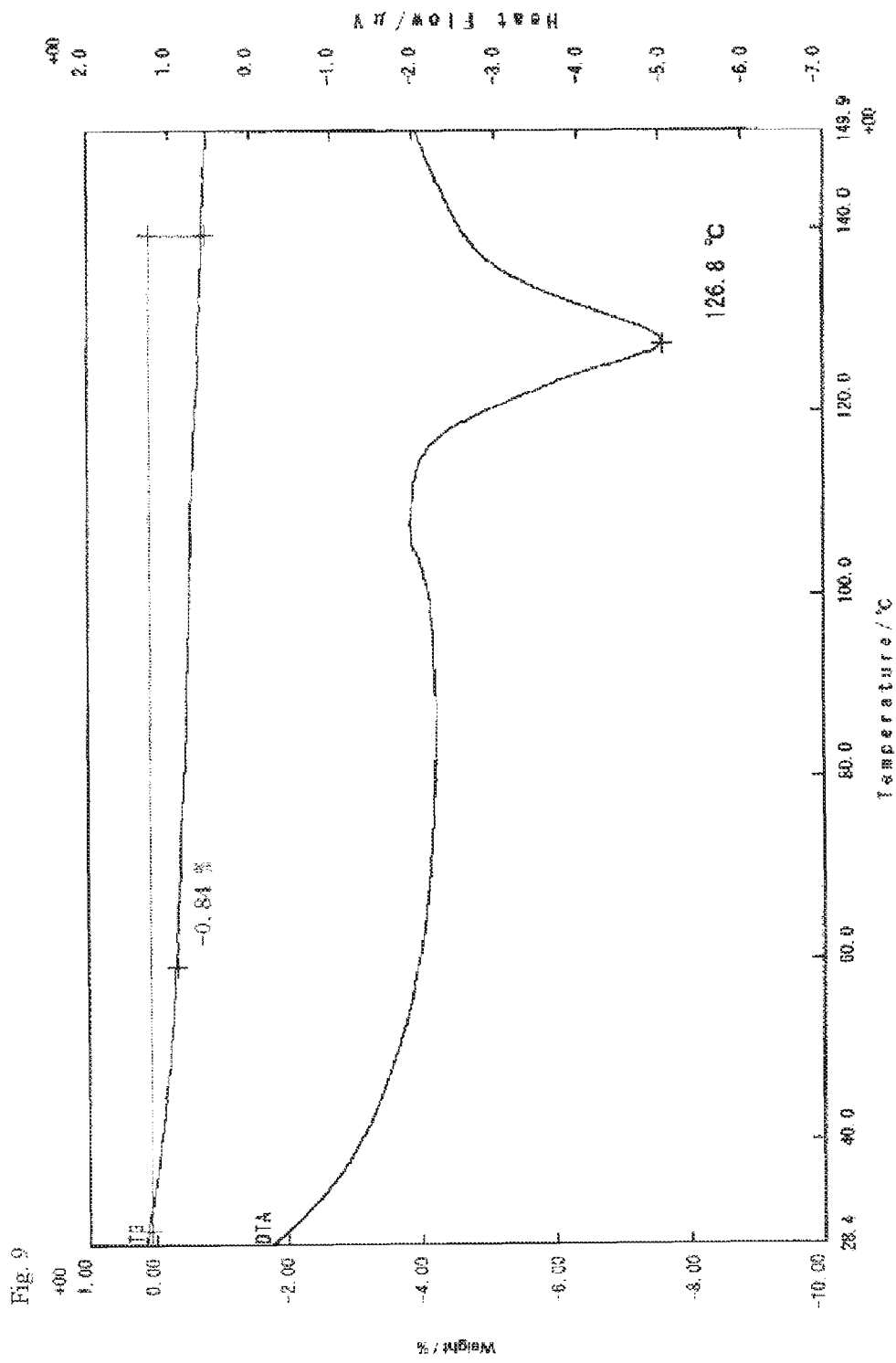
FIG. 9 shows the differential thermal analysis/thermogravimetric analysis curves of the C-form crystal.
Figure 10:
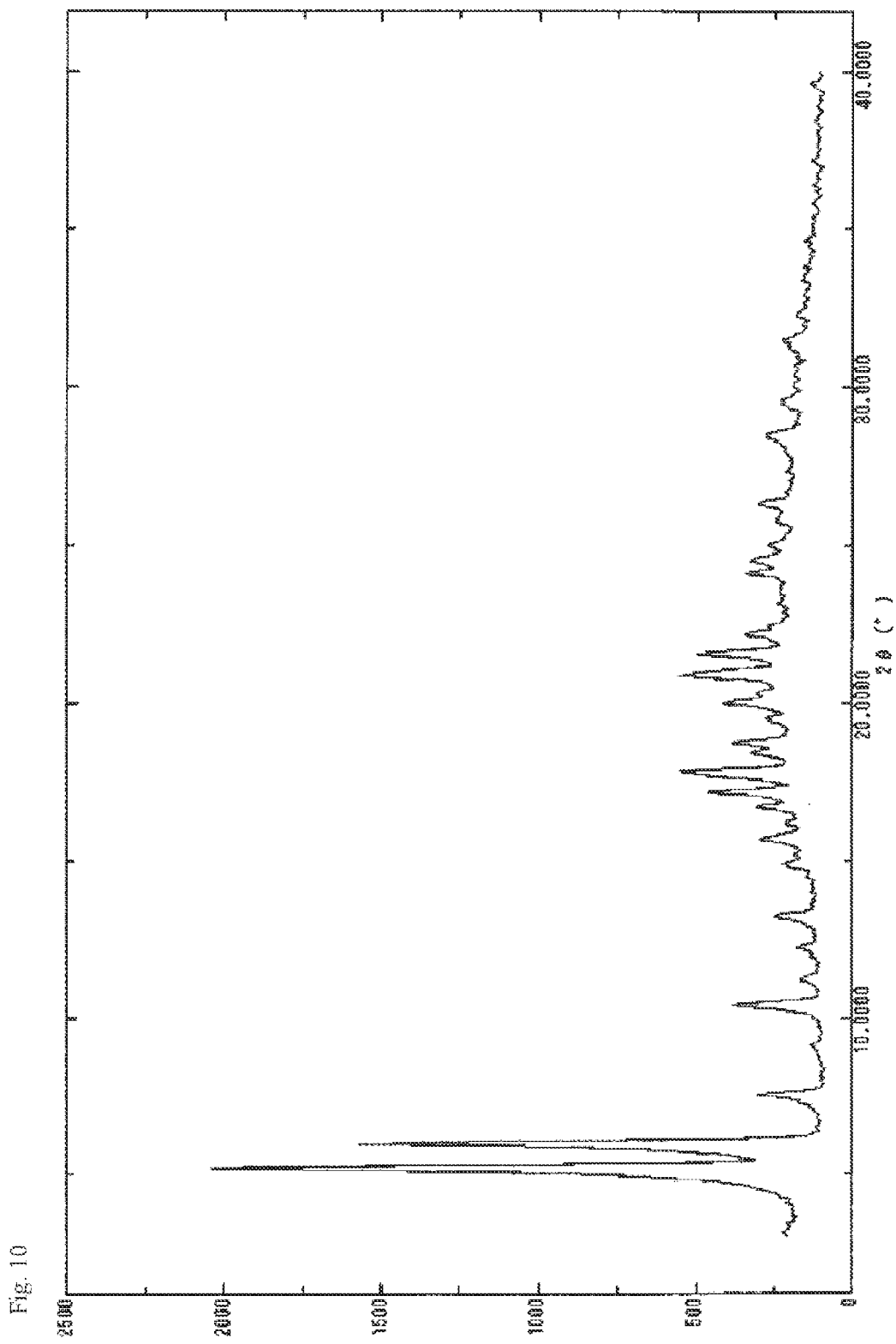
FIG. 10 shows the X-ray powder diffraction pattern of the crystal of the dihydrate.
Figure 11:
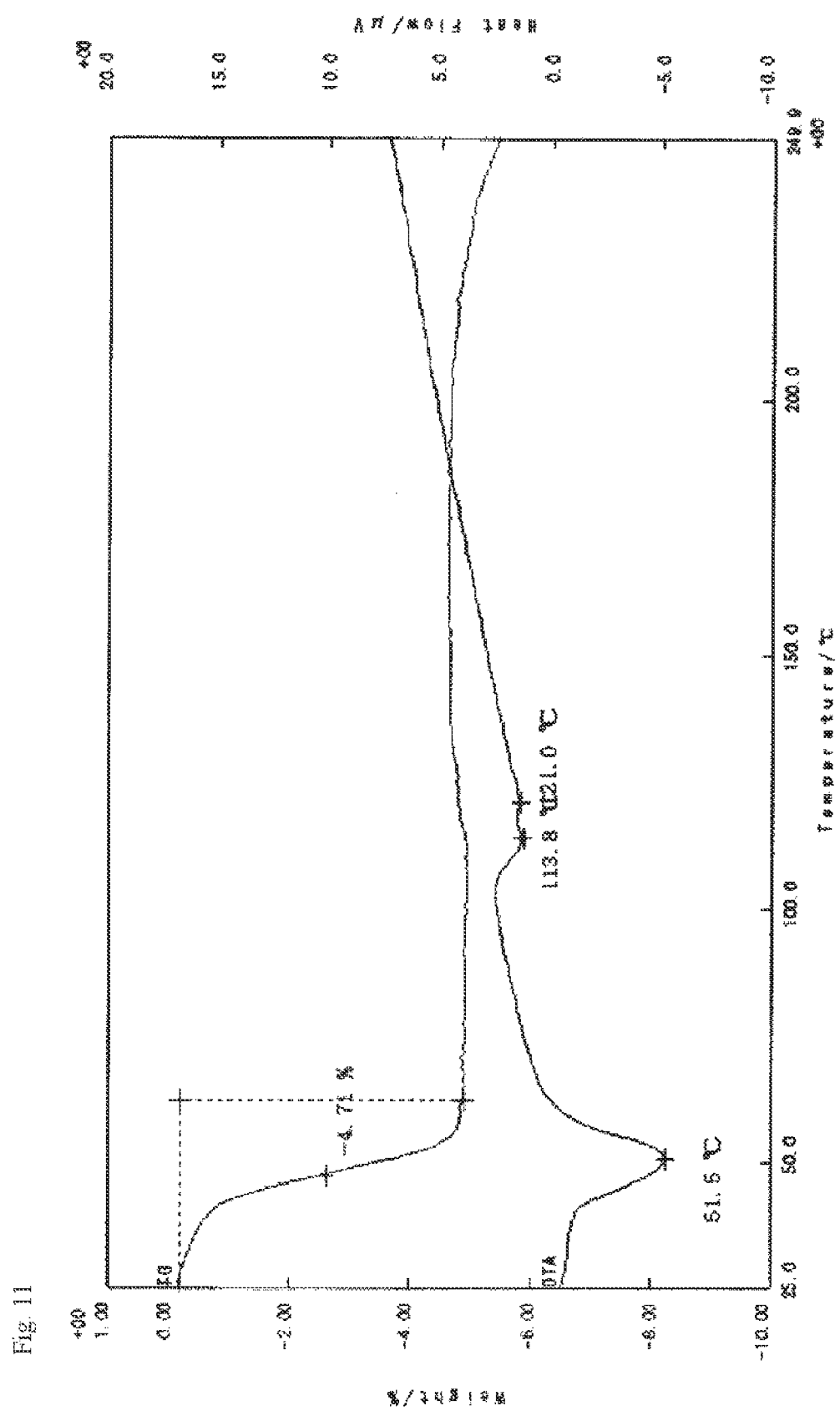
FIG. 11 shows the differential thermal analysis/thermogravimetric analysis curves of the crystal of the dihydrate.

The X-ray powder diffraction pattern of the B-form crystal of the compound (A) is as shown in FIG. 6, and the differential thermal analysis/thermogravimetric analysis curves thereof are as shown in FIG. 7.

The B-form crystal of the compound (A) is obtained by suspension of the ethanolate of the compound (A) in a mixture of isopropyl ether and an organic solvent (excluding ethanol) miscible with isopropyl ether or a mixture of hexane or heptane and an organic solvent (excluding ethanol) miscible with hexane or heptane.

Examples of the organic solvent (excluding ethanol) miscible with isopropyl ether are methanol, isopropyl alcohol, and t-butyl methyl ether.

Examples of the organic solvent (excluding ethanol) miscible with hexane or heptane are ethyl acetate, acetone, and t-butyl methyl ether.

The concentration at which the ethanolate of the compound (A) is suspended is 0.5 to 30% by mass, preferably 1 to 20% by mass, relative to the suspension.

The suspending temperature is 35° C. or lower, and normally 25° C.

The suspending time is not necessarily set to be constant, depending on the type of the solvent, the temperature, or other conditions. When the suspending temperature is 25° C., the suspending time is 1 week or longer, and normally 1 week. The conditions for suspending may be those which do not impair the suspended state of the compound (A), and the time for conversion into the B-form crystal can be shortened by raising the temperature. The end point of conversion into the B-form crystal can be confirmed by filtering off some of the crystal from the suspension, and measuring the X-ray powder diffraction pattern of this collected crystal.

The B-form crystal obtained as above is separated from the solvent, for example, by filtration or centrifugation of the dispersion (suspension), and is then dried at room temperature to 100° C.

The humidity at the time of drying at room temperature is 20% or less, and normally 11% or less.

No matter which of the above-mentioned methods is adopted, the drying time is not necessarily set to be constant, depending on the drying temperature, the crystal form of the raw material used, the particle size, or other conditions. The end point of the change in the crystal form can be confirmed by taking out some of the dried crystal, and measuring the X-ray powder diffraction pattern of the crystal taken.

By way of example, the B-form crystal of the compound (A) is obtained by separating the ethanolate of the compound (A) from the suspension in the solvent, and then exposing the separated ethanolate to the following conditions: 25° C., humidity of 11%.

As another example, the B-form crystal of the compound (A) is obtained by separating the ethanolate of the compound (A) from the suspension in the solvent, and then exposing the separated ethanolate to the following conditions: 60° C., humidity of 0%.

As another example, the B-form crystal of the compound (A) is obtained by separating the ethanolate of the compound (A) from the suspension in the solvent, and then exposing the separated ethanolate to the following conditions: 100° C.

The C-form crystal of the compound (A) has the following physical properties (a) to (b):

(a) Having peaks at 2θ=10.7 degrees, 17.9 degrees and 19.7 degrees in X-ray powder diffraction (Cu—Kα); and (b) Having a melting point in the vicinity of 127° C., preferably of 124° C. to 130° C.

The C-form crystal of the compound (A) is obtained by heating the A-form crystal of the compound (A) to a temperature ranging from room temperature to 150° C. under reduced pressure conditions, and then suspending the heated A-form crystal in a mixture of hexane and ethyl acetate.

The temperature to which the A-form crystal of the compound (A) is heated under reduced pressure conditions is room temperature to 150° C., preferably room temperature to 120° C., more preferably 120° C.

The concentration at which the A-form crystal of the compound (A) is suspended in the mixture of hexane and ethyl acetate after being heated under reduced pressure conditions is 0.5 to 30% by mass, preferably 1 to 20% by mass, relative to the suspension.

The suspending temperature is 55 to 75° C., and normally 65° C.

The suspending time is not necessarily set to be constant, depending on the type of the solvent, the temperature, or other conditions. When the suspending temperature is 65° C., the suspending time is 8 hours or longer, and normally 8 hours. The end point of conversion into the C-form crystal can be confirmed by filtering off some of the crystal from the suspension, and measuring the X-ray powder diffraction pattern of the crystal taken.

The C-form crystal obtained as above is separated from the solvent, for example, by distilling off the solvent by means of a rotary evaporator, or by filtration or centrifugation of the dispersion (suspension), and is then dried at 35° C. or lower, normally at room temperature.

No matter which of the above-mentioned methods is adopted, the drying time is not necessarily set to be constant, depending on the drying temperature, the crystal form of the raw material used, the particle size, or other conditions. The end point of the change in the crystal form can be confirmed by taking out a part of the dried crystal, and measuring the X-ray powder diffraction pattern of the crystal taken.

The crystal of the dihydrate of the compound (A) has the following physical properties (a) to (b):

(a) Having peaks at 2θ=17.2 degrees, 17.8 degrees and 20.9 degrees in X-ray powder diffraction (Cu—Kα); and (b) Having a melting point in the vicinity of 121° C., preferably of 118° C. to 124° C.

The above crystal is obtained by suspending the ethanolate of the compound (A) in a mixture of isopropyl ether and methanol.

The concentration at which the ethanolate of the compound (A) is suspended is 0.5 to 20% by mass, preferably 0.5 to 10% by mass, relative to the suspension.

The suspending temperature is 35° C. or lower, and normally 25° C.

The suspending time is not necessarily set to be constant, depending on the type of the solvent, the temperature, or other conditions. When the suspending temperature is 25° C., the suspending time is 6 days or more, and normally 6 days. The conditions for suspending may be those which do not impair the suspended state of the compound (A), and the time for conversion into the crystal of the dihydrate can be shortened by raising the temperature. The end point of conversion into the crystal of the dihydrate can be confirmed by filtering off some of the crystal from the suspension, and measuring the X-ray powder diffraction pattern of the crystal taken.

The crystal of the dihydrate obtained as above is separated from the solvent, for example, by filtration or centrifugation of the dispersion (suspension), and is then dried at room temperature.

The humidity at the time of drying at room temperature is 40% to 85%. It has been confirmed that the crystal of the dihydrate is transformed from the B-form crystal under conditions involving a humidity of 40% or higher, and that the crystal of the dihydrate deliquesces at a humidity of 85% or higher.

No matter which of the above-mentioned methods is adopted, the drying time is not necessarily set to be constant, depending on the drying temperature, the crystal form of the raw material used, the particle size, or other conditions. The end point of the change in the crystal form can be confirmed by taking out some of the dried crystal, and measuring the X-ray powder diffraction pattern of the crystal taken.

EXAMPLES

Next, the present invention will be described in further detail by Reference Examples, Examples and Test Examples, but the present invention is in no way limited to their contents.

The NMR (nuclear magnetic resonance) spectra were measured at 200 MHz (GEMINI2000/200, Varian Instruments), 300 MHz (INOVA 300, Varian Instruments, JEOL JNM-ECP300, JEOL Ltd., JEOL JNM-ECX300, JEOL Ltd.), and 600 MHz (JEOL JNM-ECA600, JEOL Ltd.) at room temperature. The chemical shift values herein were indicated by the parts per million (δ) values relative to an internal standard material (tetramethylsilane).

The mass spectra were measured using Waters micromass GCT (EI: electron ionization), micromass Platform-LC mass spectrometer (ESI: electrospray ionization) or Shimadzu LCMS-2010EV (ESI: electrospray ionization/APCI: atmospheric pressure chemical ionization, dual-mode ionization).

The elemental analysis was carried out using PerkinElmer 2400Z.

The powder X-ray spectra were measured with Rigaku RINT2200UltimaIII.

The differential thermal analysis/thermogravimetric analysis (TG/DTA) were carried out using Rigaku Thermo plus EvoTG8120.

For silica gel column chromatography, "Silica Gel 60" or "Silica Gel 60N" of KANTO CHEMICAL CO., INC. was used.

Room temperature refers to 25° C.

Reference Example 1

Production of Intermediate (B)

[Formula 2]

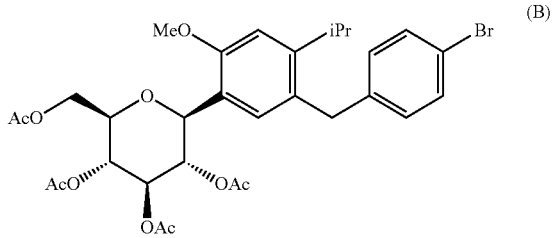

Reference Example 1-1

Compound (B1)

[Formula 3]

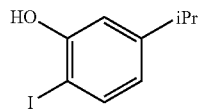

To an acetic acid (200 mL) solution of 3-isopropylphenol (25 g, 0.184 mol), an aqueous suspended solution (75 mL) of potassium iodate (7.88 g, 0.0368 mol) and iodine (18.7 g, 0.0736 mol) were added, and the resulting reaction solution was stirred for 20 hours at room temperature. After diethyl ether (400 mL) and water (300 mL) were added, the organic layer was separated. The organic layer was washed with water, a saturated aqueous solution of sodium hydrogen carbonate, and brine, and then dried over anhydrous magnesium sulfate. The desiccant was filtered out, and then the solvent was distilled off under reduced pressure. The resulting residue was purified by neutral silica gel column chromatography (hexane:ethyl acetate=95:5) to obtain a colorless oily compound (B1) (27.6 g, 57%).

$^1$H NMR (200 MHz, CHLOROFORM-d) δ ppm 1.16-1.25 (m, 6H) 2.64-2.98 (m, 1H) 5.21 (s, 1H) 6.57 (dd, J=8.13, 2.20 Hz, 1H) 6.88 (d, J=2.20 Hz, 1H) 7.54 (d, J=8.13 Hz, 1H).

Reference Example 1-2

Compound (B2)

[Formula 4]

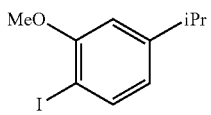

Methyl iodide (9.8 mL, 0.156 mol) was added to an acetonitrile suspension (200 mL) of the compound (B1) (27.4 g, 0.104 mol) and potassium carbonate (21.7 g, 0.156 mol), and the mixture was stirred for 2.5 hours at 40° C. Methyl iodide (3.5 mL, 0.052 mol) was further added, and the mixture was stirred for 1 hour at the same temperature. Insolubles were filtered out, and the filtrate was diluted with ethyl acetate. The organic layer was washed with water, a 10% aqueous solution of sodium thiosulfate, and brine, and dried over anhydrous magnesium sulfate. The desiccant was filtered out, and then the solvent was distilled off under reduced pressure. The resulting residue was purified by neutral silica gel column chromatography (hexane→hexane:ethyl acetate=95:5) to obtain a light yellow oily compound (B2) (24.5 g, 85%).

$^1$H NMR (300 MHz, CHLOROFORM-d) δ ppm 1.24 (d, J=6.84 Hz, 6H) 2.87 (quin, J=6.92 Hz, 1H) 3.88 (s, 3H) 6.58-6.65 (m, 1H) 6.70 (d, J=1.87 Hz, 1H) 7.65 (d, J=8.08 Hz, 1H). MS ESI/APCI Dual posi: 277[M+H]$^+$.

Reference Example 1-3

Compound (B3)

[Formula 5]

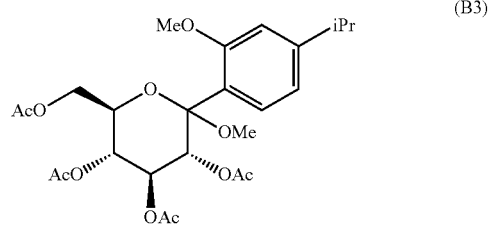

To a THF (100 mL) solution of the compound (B2) (24.5 g, 88.6 mmol), a 2.6M n-butyllithium solution in hexane (34 mL, 88.6 mmol) was added dropwise at −78° C. under a nitrogen atmosphere, and the mixture was stirred for 5 minutes at the same temperature. Then, a THF (60 mL) solution of 2,3,4,6-tetra-O-trimethylsilyl-D-glucono-1,5-lactone (37.6 g, 80.5 mmol) was added dropwise over 25 minutes, and the mixture was stirred for 10 minutes at the same temperature. Ice and water were added to the reaction solution, and the resulting mixture was warmed to room temperature and then extracted with ethyl acetate. The organic layer combined was washed with brine, and dried over anhydrous magnesium sulfate. The desiccant was filtered out, and then the solvent was distilled off under reduced pressure.

The resulting residue was dissolved in a methanol (380 mL) solution containing methanesulfonic acid (1.55 g, 16.1 mmol), and the solution was stirred for 2 hours at room temperature. Then, the solution was neutralized with triethylamine (11.2 mL, 80.5 mmol), and the reaction mixture was concentrated.

The resulting residue (30.2 g) was dissolved in pyridine (100 mL), and acetic anhydride (100 mL) was added, followed by stirring the mixture for 14 hours at room temperature. Iced water (400 mL) was added, and the mixture was extracted twice with ethyl acetate (200 mL). The organic layer combined was washed with 1M hydrochloric acid, a saturated aqueous solution of sodium hydrogen carbonate, and brine, and dried over anhydrous magnesium sulfate. The desiccant was filtered out, and then the solvent was distilled off under reduced pressure. The resulting residue was purified by neutral silica gel column chromatography (hexane→hexane:ethyl acetate=6:4) to obtain a light yellow oily compound (B3) (32.8 g, 80%; 3 steps).

¹H NMR (300 MHz, CHLOROFORM-d) δ ppm 1.23 (d, 6H) 1.84 (s, 3H) 1.97 (s, 3H) 2.06 (s, 3H) 2.10 (s, 3H) 2.87 (dt, J=13.83, 6.92 Hz, 1H) 3.32 (s, 3H) 3.87 (s, 3H) 4.04 (ddd, J=10.26, 4.74, 2.41 Hz, 1H) 4.17-4.23 (m, 1H) 4.28-4.36 (m, 1H) 5.25 (dd, J=10.18, 9.40 Hz, 1H) 5.36 (d, J=10.10 Hz, 1H) 5.60 (dd, J=10.03, 9.40 Hz, 1H) 6.74 (d, J=1.55 Hz, 1H) 6.79 (dd, J=8.08, 1.24 Hz, 1H) 7.26-7.33 (m, 1H).

MS ESI/APCI Dual posi: 533[M+Na]⁺.

Reference Example 1-4

Compound (B4)

[Formula 6]

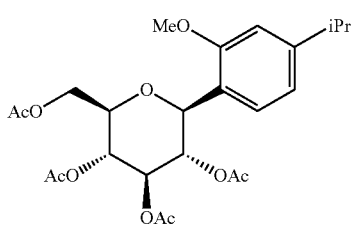

To a solution of the compound (B3) (32.8 g, 64.0 mmol) in chloroform (150 mL) and acetonitrile (150 mL), Et₃SiH (21 mL, 128 mmol) and BF₃.OEt₂ (49 mL, 385 mmol) were added at 4° C. under a nitrogen atmosphere, and the mixture was stirred for 1 hour at the same temperature. A saturated aqueous solution of sodium hydrogen carbonate was added to the reaction solution, and the mixture was extracted with chloroform. Then, the organic layer was washed with brine, and dried over anhydrous magnesium sulfate. The desiccant was filtered out, and then the solvent was distilled off under reduced pressure. The resulting residue was purified by neutral silica gel column chromatography (hexane:ethyl acetate=2:1) to obtain a light yellow gummy compound (B4) (22.9 g, 74%).

¹H NMR (300 MHz, CHLOROFORM-d) δ ppm 1.22 (d, J=6.99 Hz, 6H) 1.77 (s, 3H) 2.01 (s, 3H) 2.05 (s, 3H) 2.07 (s, 3H) 2.87 (dt, J=13.76, 6.96 Hz, 1H) 3.80-3.87 (m, 1H) 3.84 (s, 3H) 4.09-4.16 (m, 1H) 4.22-4.29 (m, 1H) 4.88-4.95 (m, 1H) 5.18-5.27 (m, 1H) 5.32-5.38 (m, 2H) 6.71 (d, J=1.55 Hz, 1H) 6.83 (dd, J=7.93, 1.55 Hz, 1H) 7.23-7.30 (m, 1H).

MS ESI/APCI Dual posi: 503[M+Na]⁺.
MS ESI/APCI Dual nega: 515[M+Cl]⁻.

Reference Example 1-5

Compound (B5)

[Formula 7]

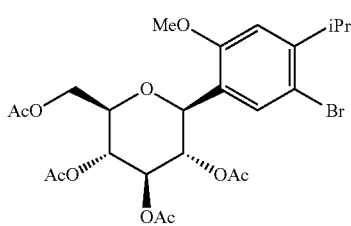

To an acetic acid (90 mL) solution of the compound (B4) (22.9 g, 47.7 mmol), bromine (2.4 mL, 47.6 mmol) was added dropwise at room temperature. The reaction mixture was stirred for 1 hour, and the resulting reaction mixture was added to a saturated aqueous solution of sodium hydrogen carbonate (400 mL). The mixture was extracted twice with ethyl acetate, and the organic layer combined was washed with a 10% aqueous solution of sodium chloride, and dried over anhydrous magnesium sulfate. The desiccant was filtered out, and then the solvent was distilled off under reduced pressure. The resulting residue was purified by neutral silica gel column chromatography (hexane:ethyl acetate=3:2) to obtain a light yellow amorphous compound (B5) (25.5 g, 96%).

¹H NMR (300 MHz, CHLOROFORM-d) δ ppm 1.20 (d, J=6.84 Hz, 3H) 1.23 (d, J=6.84 Hz, 3H) 1.80 (s, 3H) 2.01 (s, 3H) 2.05 (s, 3H) 2.09 (s, 3H) 3.31 (quin, J=6.84 Hz, 1H) 3.77-3.82 (m, 1H) 3.83 (s, 3H) 4.10-4.17 (m, 1H) 4.22-4.30 (m, 1H) 4.83 (d, J=9.48 Hz, 1H) 5.17-5.38 (m, 3H) 6.75 (s, 1H) 7.49 (s, 1H).

MS ESI/APCI Dual posi: 581[M+Na]⁺, 583[M+2+Na]⁺.

Reference Example 1-6

Compound (B6)

[Formula 8]

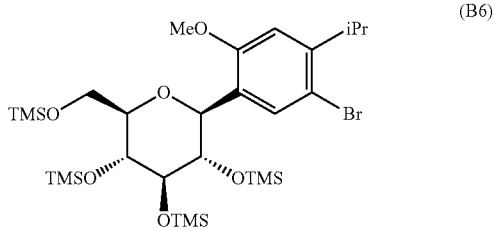

To a methanol (250 mL) suspension of the compound (B5) (25.5 g, 45.6 mmol), a wt. % sodium methoxide-methanol solution (1 mL, 4.9 mmol) was added, and the mixture was stirred for 2 hours at room temperature. Dry ice was added to the reaction solution, and then the solvent was distilled off under reduced pressure. The resulting residue was dissolved in N,N-dimethylformamide (135 mL) and, under ice cooling, triethylamine (45 mL) and chlorotrimethylsilane (35 mL) were added. The reaction mixture was stirred for 2 hours at room temperature, and iced water was added. The mixture was extracted twice with toluene, and the organic layer combined was washed with brine, and dried over anhydrous magnesium sulfate. The desiccant was filtered out, and then the solvent was distilled off under reduced pressure to obtain a brown oily compound (B6) (30.3 g). This compound was used for a next reaction without purification.

¹H NMR (300 MHz, CHLOROFORM-d) δ ppm −0.32 (s, 9H) 0.09 (s, 9H) 0.18 (s, 9H) 0.20 (s, 9H) 1.19 (d, J=6.84 Hz, 3H) 1.23 (d, J=6.84 Hz, 3H) 3.26-3.44 (m, 3H) 3.52-3.58 (m, 2H) 3.65-3.75 (m, 3H) 3.76-3.83 (m, 1H) 3.80 (s, 3H) 4.60 (d, J=8.55 Hz, 1H) 6.72 (s, 1H) 7.51 (s, 1H).

MS ESI/APCI Dual posi: 701[M+Na]⁺, 703[M+2+Na]⁺.

Reference Example 1-7

Compound (B7)

[Formula 9]

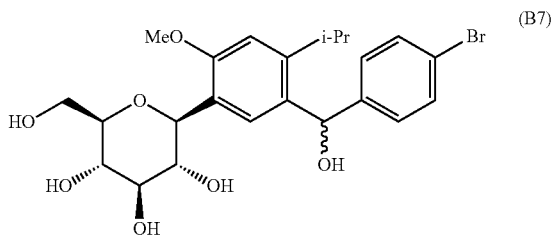

(B7)

To a THF (40 mL) solution of the compound (B6) (8.7 g, 12.9 mmol), a 2.7M n-butyllithium hexane solution (4.7 mL, 12.9 mmol) was added dropwise at −78° C. under an argon atmosphere, and the mixture was stirred for 10 minutes at the same temperature. Then, a THF (25 mL) solution of 4-bromobenzaldehyde (2.6 g, 14.2 mmol) was added dropwise over 15 minutes, and the mixture was stirred for 30 minutes at the same temperature. A saturated aqueous solution of ammonium chloride was added to the reaction mixture and, after the mixture was warmed to room temperature, the warmed mixture was extracted twice with ethyl acetate. The organic layer combined was washed with brine, and dried over anhydrous magnesium sulfate. The desiccant was filtered out, and then the solvent was distilled off under reduced pressure.

The resulting residue was dissolved in a methanol (65 mL) solution containing methanesulfonic acid (0.2 g), and the solution was stirred for 14 hours at room temperature. The reaction mixture was neutralized with triethylamine (1.8 mL), and the reaction mixture was concentrated. The resulting residue was purified by acidic silica gel column chromatography (chloroform→chloroform:methanol=9:1) to obtain a colorless amorphous compound (B7) (2.9 g, 45%).

$^1$H NMR (300 MHz, METHANOL-$d_4$) δ ppm 1.00-1.11 (m, 6H) 3.10-3.27 (m, 2H) 3.34-3.40 (m, 5H) 3.43-3.70 (m, 4H) 3.84 (s, 4H) 4.66 (d, J=9.64 Hz, 1H) 5.47 (s, 1H) 6.89 (d, J=1.24 Hz, 1H) 7.20 (d, J=2.18 Hz, 1H) 7.22 (d, J=2.18 Hz, 1H) 7.37-7.47 (m, 3H).

MS ESI/APCI Dual posi: 479[M−H2O+H]$^+$

Reference Example 1-8

Production of Intermediate (B)

[Formula 10]

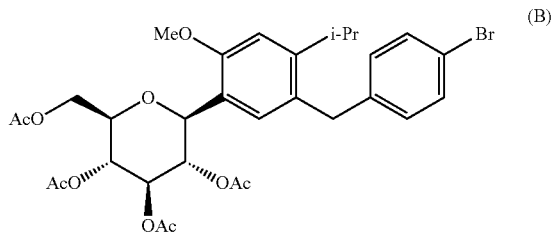

(B)

The compound (B7) (2.9 g, 5.8 mmol) was dissolved in pyridine (18 mL). Acetic anhydride (9 mL) was added to the resulting solution, and the mixture was stirred for 5 hours at room temperature. Iced water was added, and the mixture was extracted twice with ethyl acetate. The organic layer combined was washed with 3N hydrochloric acid and brine, and dried over anhydrous magnesium sulfate. The desiccant was filtered out, and then the solvent was distilled off under reduced pressure to obtain a crude product (3.3 g).

To a solution of this crude product (3.3 g) in chloroform (25 mL) and acetonitrile (25 mL), Et$_3$SiH (1.1 mL, 7.1 mmol) was added, and the mixture was cooled with ice under a nitrogen atmosphere. Under ice cooling, BF$_3$.OEt$_2$ (0.9 mL, 7.1 mmol) was added dropwise over 10 minutes, and the mixture was stirred for 30 minutes at the same temperature. A saturated aqueous solution of sodium hydrogen carbonate was added to the reaction mixture, and the mixture was extracted with chloroform. Then, the organic layer was washed with brine, and dried over anhydrous magnesium sulfate. The desiccant was filtered out, and then the solvent was distilled off under reduced pressure. The resulting residue was purified by acidic silica gel column chromatography (hexane:ethyl acetate=9:1→6:4) to obtain an intermediate (B) as a colorless oil (2.9 g, 76%).

$^1$H NMR (300 MHz, CHLOROFORM-d) δ ppm 1.04 (d, J=6.84 Hz, 3H) 1.09 (d, J=6.84 Hz, 3H) 1.76 (s, 3H) 2.01 (s, 3H) 2.05 (s, 3H) 2.06 (s, 3H) 2.91-3.06 (m, 1H) 3.80-3.88 (m, 4H) 3.91 (d, J=5.13 Hz, 2H) 4.06-4.18 (m, 1H) 4.20-4.31 (m, 1H) 4.82-4.93 (m, 1H) 5.15-5.43 (m, 3H) 6.77 (s, 1H) 6.92 (d, J=8.55 Hz, 2H) 7.11 (s, 1H) 7.36 (d, J=8.55 Hz, 2H).

MS ESI/APCI Dual posi: 671[M+Na]$^+$, 666[M+NH$_4$]$^+$

Reference Example 2

Production of Intermediate (C)

[Formula 11]

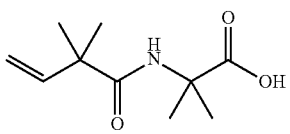

(C)

Reference Example 2-1

Compound (C1)

[Formula 12]

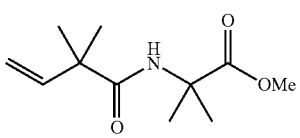

(C1)

To a chloroform (250 mL) solution of 2,2-dimethyl-3-butenoic acid (J. Org. Chem., Vol. 65, p. 8402, 2000) (5.42 g, 47.5 mmol), oxalyl chloride (4.43 mL, 49.9 mmol) and N,N-dimethylformamide (3 drops) were added under a nitrogen atmosphere, and the mixture was stirred for 1.5 hours at room temperature. Then, the reaction mixture was cooled with ice, and triethylamine (19.9 mL, 143 mmol) and α-aminoisobutyric acid methyl ester hydrochloride (10.9 g, 71.2 mmol) were added, followed by stirring the mixture for 1 hour at room temperature. Water was added to the reaction mixture, and the mixture was extracted with chloroform. Then, the organic layer was washed with 3M hydrochloric acid, a saturated aqueous solution of sodium hydrogen carbonate, and brine, and dried over anhydrous magnesium sulfate. The desiccant was filtered out, and then the solvent was distilled off under reduced pressure. The resulting residue was purified by silica gel column chromatography (hexane→hexane:ethyl acetate=4:1) to obtain a colorless powdery compound (C1) (9.38 g, 93%).

$^1$H NMR (300 MHz, CHLOROFORM-d) δ ppm 1.27 (s, 6H) 1.51 (s, 6H) 3.73 (s, 3H) 5.17-5.32 (m, 2H) 6.02 (dd, J=17.56, 10.57 Hz, 1H) 6.25 (br. s., 1H).

MS ESI/APCI Dual posi: 214[M+H]$^+$.

Reference Example 2-2

Intermediate (C)

[Formula 13]

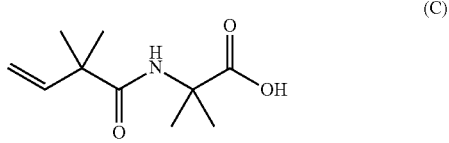

A 4M aqueous solution of sodium hydroxide (16.5 mL, 66.0 mmol) was added to a methanol (20 mL) solution of the compound (C1) (9.38 g. 43.9 mmol), and the mixture was stirred for 1 hour at room temperature. Then, the reaction mixture was concentrated. The resulting residue was dissolved in water, and the solution was neutralized with the addition of 3M hydrochloric acid. The mixture was extracted twice with ethyl acetate, and the organic layer combined was washed with brine, and dried over anhydrous magnesium sulfate. The desiccant was filtered out, and then the solvent was distilled off under reduced pressure to obtain a colorless powdery intermediate (C) (8.19 g, 94%).

$^1$H NMR (300 MHz, CHLOROFORM-d) δ ppm 1.29 (s, 6H) 1.54 (s, 6H) 5.16-5.36 (m, 2H) 6.01 (dd, J=17.49, 10.65 Hz, 1H) 6.14 (s, 1H).

MS ESI/APCI Dual posi: 200[M+H]$^+$, 222[M+Na]$^+$.

MS ESI/APCI Dual nega: 198[M−H]$^-$.

Reference Example 3

Production of Compound (D)

[Formula 14]

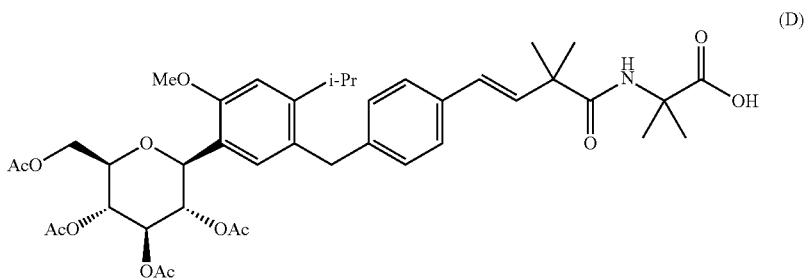

Under an argon atmosphere, an acetonitrile (36 mL) suspension of the intermediate (B) (1.2 g, 1.85 mmol), the intermediate (C) (2.59 g, 13.0 mmol), palladium(II) acetate (44 mg, 0.19 mmol), tri-o-tolylphosphine (112 mg, 0.37 mmol), and triethylamine (1.3 mL, 9.25 mmol) was stirred for 30 minutes at 120° C. under microwave irradiation. The reaction mixture was filtered using Celite (registered trademark), and washed with ethyl acetate. The filtrate was concentrated under reduced pressure, and the resulting residue was purified by neutral silica gel column chromatography (chloroform→chloroform:methanol=9:1) to obtain a compound (D) as a partially purified product (1.5 g). The resulting compound (D) (1.5 g) was further purified by neutral silica gel column chromatography (hexane:ethyl acetate=7:3→2:8) to obtain a light yellow amorphous compound (D) (854 mg, 60%).

$^1$H NMR (300 MHz, CHLOROFORM-d) δ ppm 1.08 (d, J=6.84 Hz, 3H) 1.12 (d, J=6.84 Hz, 3H) 1.38 (s, 6H) 1.53 (s, 6H) 1.77 (s, 3H) 2.00 (s, 3H) 2.05 (s, 6H) 3.06 (quin, J=6.64 Hz, 1H) 3.78-3.83 (m, 1H) 3.84 (s, 3H) 3.97 (s, 2H) 4.07-4.18 (m, 1H) 4.17-4.27 (m, 1H) 4.87 (dd, J=6.76, 2.88 Hz, 1H) 5.16-5.25 (m, 1H) 5.27-5.40 (m, 2H) 6.18-6.33 (m, 2H) 6.54 (d, J=16.48 Hz, 1H) 6.77 (s, 1H) 7.03 (d, J=8.08 Hz, 2H) 7.10 (s, 1H) 7.29 (d, J=8.08 Hz, 2H).

MS ESI/APCI Dual posi: 768[M+H]$^+$, 790[M+Na]$^+$.

MS ESI/APCI Dual nega: 766[M−H]$^-$.

Reference Example 4 Production of Compound (E)

[Formula 15]

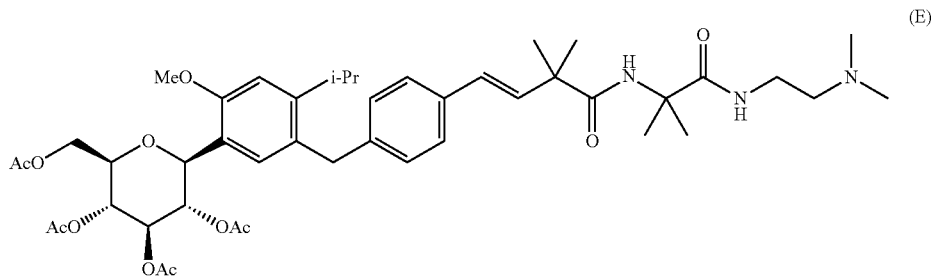

To a chloroform (1.5 mL)/N,N-dimethylformamide (1.5 mL) solution of the compound (D) (100 mg, 0.13 mmol), 1-hydroxybenzotriazole monohydrate (HOBt.H$_2$O) (30 mg, 0.20 mmol), and N,N-dimethylethylenediamine (42 μL, 0.39 mmol), N-ethyl-N'-3-dimethylaminopropylcarbodiimide hydrochloride (EDC-HCl) (37 mg, 0.20 mmol) was added, and the mixture was stirred overnight at room temperature. The reaction mixture was poured into water, and the mixture was extracted twice with ethyl acetate. The organic layer combined was washed with brine, and dried over anhydrous magnesium sulfate. The desiccant was filtered out, and then the solvent was distilled off under reduced pressure. The resulting residue was purified by neutral silica gel column chromatography (hexane:ethyl acetate=7:3→2:8) to obtain a colorless amorphous compound (E) (103 mg, 94%).

$^1$H NMR (300 MHz, CHLOROFORM-d) δ ppm 1.05 (d, J=6.84 Hz, 3H) 1.10 (d, J=6.84 Hz, 3H) 1.38 (s, 6H) 1.49 (s, 6H) 1.77 (s, 3H) 2.00 (s, 3H) 2.05 (s, 3H) 2.06 (s, 3H) 2.46 (s, 6H) 2.64-2.78 (m, 2H) 3.04 (quin, J=6.80 Hz, 1H) 3.38-3.49 (m, 2H) 3.78-3.83 (m, 1H) 3.85 (s, 3H) 3.87-4.04 (m, 2H) 4.08-4.18 (m, 1H) 4.18-4.30 (m, 1H) 4.87 (d, J=9.48 Hz, 1H) 5.16-5.27 (m, 1H) 5.28-5.44 (m, 2H) 6.35 (s, 1H) 6.40-6.57 (m, 2H) 6.77 (s, 1H) 7.01 (d, J=8.24 Hz, 2H) 7.13 (s, 1H) 7.32 (d, J=8.24 Hz, 2H) 7.40 (s, 1H).

MS ESI/APCI Dual posi: 838[M+H]$^+$.
MS ESI/APCI Dual nega: 872[M+Cl]$^-$.

Reference Example 5

Production of Compound (A)

A triethylamine/water/methanol mixture (1/1/5, 2.5 mL) was added to the compound (E) (103 mg, 0.12 mmol). The reaction mixture was stirred for 17 hours at room temperature, and the solvent was distilled off under reduced pressure. The resulting residue was purified by neutral silica gel column chromatography (chloroform→chloroform:methanol=8:2) to obtain a colorless amorphous compound (A) (62.1 mg, 75%).

$^1$H NMR (600 MHz, METHANOL-d$_4$) δ ppm 1.07 (d, J=5.04 Hz, 3H) 1.09 (d, J=5.04 Hz, 3H) 1.36 (s, 6H) 1.44 (s, 6H) 2.23 (s, 6H) 2.41 (t, J=6.88 Hz, 2H) 3.10 (quin, J=6.76 Hz, 1H) 3.26-3.30 (m, 2H) 3.38 (d, J=5.96 Hz, 2H) 3.45-3.52 (m, 1H) 3.54-3.60 (m, 1H) 3.62-3.69 (m, 1H) 3.79-3.89 (m, 4H) 3.99 (s, 2H) 4.65 (d, J=9.63 Hz, 1H) 6.39 (d, J=16.51 Hz, 1H) 6.52 (d, J=16.51 Hz, 1H) 6.88 (s, 1H) 7.07 (d, J=8.25 Hz, 2H) 7.23 (s, 1H) 7.31 (d, J=8.25 Hz, 2H).

MS ESI/APCI Dual posi: 670[M+H]$^+$.
MS ESI/APCI Dual nega: 704[M+Cl]$^-$.
Anal. Calcd for C$_{37}$H$_{55}$N$_3$O$_8$·1.0H$_2$O: C, 64.6; H, 8.36; N, 6.11. Found: C, 64.5; H, 8.31; N, 6.02.

Reference Example 6

Purification of Compound (A)

The colorless amorphous compound (A) (9.88 g, purity 96.0%) was purified by neutral silica gel column chromatography (chloroform:methanol=7:3→1:1) to obtain a colorless amorphous compound (A) (6.24 g, recovery 63%, purity 99.5%). The colorless amorphous compound (A) (6.24 g, purity 99.5%) was further purified by neutral silica gel col-

[Formula 16]

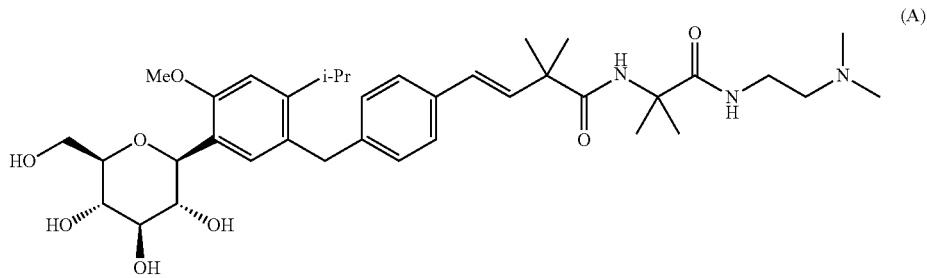

umn chromatography (chloroform:methanol=7:3→3:7) to obtain a colorless amorphous compound (A) (3.31 g, recovery 53%, purity 99.9%).

Example 1

Twenty-five milligrams of the colorless amorphous compound (A) (purity 99.9%) was dissolved in 0.08 mL of ethanol at room temperature, and then the solution was stirred for 1 day at room temperature to obtain a crystal. The crystal was dried under reduced pressure at room temperature to give 27 mg of a colorless crystal (recovery 100%). The X-ray powder diffraction pattern and the differential thermal analysis/thermogravimetric analysis (TG/DTA) of the resulting crystal showed that it was a crystal of an ethanolate of the compound (A).

Example 2

Fifty-six grams of the colorless amorphous compound (A) (purity 96.0%) was dissolved in 135 mL of ethanol at 66° C. To the stirred solution was added heptane and then cooled. At about 45° C., the crystal of the ethanolate of the compound (A) obtained in Example 1 was added, and then the solution was cooled to 1° C. The crystal precipitated was collected by filtration, and then dried under reduced pressure at 40° C. to give 46 g of a colorless crystal (recovery 82%, purity 99.1%). The X-ray powder diffraction pattern, differential thermal analysis/thermogravimetric analysis (TG/DTA), and infrared absorption spectrum of the resulting crystal showed that it was a crystal of an ethanolate of the compound (A).

$^1$H NMR (600 MHz, METHANOL-$d_4$) δ ppm 1.06 (d, J=5.04 Hz, 3H) 1.07 (d, J=5.50 Hz, 3H) 1.15 (t, J=6.88 Hz, 3H) 1.34 (s, 6H) 1.43 (s, 6H) 2.20 (s, 6H) 2.37 (t, J=6.88 Hz, 2H) 3.08 (quin, J=6.88 Hz, 1H) 3.26 (t, J=6.88 Hz, 2H) 3.28-3.30 (m, 4H) 3.34-3.38 (m, 2H) 3.43-3.49 (m, 1H) 3.55 (t, J=9.17 Hz, 1H) 3.58 (q, J=6.88 Hz, 2H) 3.62-3.66 (m, 1H) 3.78-3.85 (m, 4H) 3.96 (s, 2H) 4.63 (d, J=9.62 Hz, 1H) 6.37 (d, J=16.50 Hz, 1H) 6.50 (d, J=16.50 Hz, 1H) 6.86 (s, 1H) 7.05 (d, J=7.80 Hz, 2H) 7.22 (s, 1H) 7.29 (d, J=7.79 Hz, 2H).

MS ESI/APCI Dual posi: 670[M+H]$^+$.
MS ESI/APCI Dual nega: 704[M+Cl]$^-$.
Anal. Calcd for $C_{39}H_{61}N_3O_9 \cdot 0.6H_2O$: C, 64.94; H, 8.61; N, 5.83. Found: C, 64.75; H, 8.46; N, 5.82.

Example 3

To 0.10 g of the ethanolate of the compound (A) was added 600 µL of a phosphate buffer solution (a mixed solution of sodium dihydrogen phosphate dihydrate and disodium hydrogen phosphate dodecahydrate) (pH 6.8), and the mixture was suspended for 24 hours at 25° C. After centrifugation (3000 rpm, 25° C., 10 minutes), the supernatant was removed, and the residue was dried at room temperature to obtain a colorless crystal. The X-ray powder diffraction pattern, and differential thermal analysis/thermogravimetric analysis (TG/DTA) of the resulting crystal showed that it was an A-form crystal.

Example 4

To 0.10 g of the ethanolate of the compound (A) was added 2 mL of isopropyl ether/methanol (9/1), and the suspension was stirred for 1 week at 25° C. After centrifugation (3000 rpm, 25° C., 10 minutes), the supernatant was removed, and the residue was dried at room temperature to obtain a colorless crystal. The X-ray powder diffraction pattern and differential thermal analysis/thermogravimetric analysis (TG/DTA) of the resulting crystal showed that it was a B-form crystal.

Example 5

After 1.00 g of the A-form crystal of the compound (A) was heated to 120° C. under reduced pressure, 0.5 g of the crystal was taken. The crystal was suspended in 10 mL of hexane/ethyl acetate (2/1), and the suspension was stirred for 8 hours at 65° C. The solvents of the suspension were distilled off, and the residue was dried at room temperature to obtain a colorless crystal. The X-ray powder diffraction pattern and differential thermal analysis/thermogravimetric analysis (TG/DTA) of the resulting crystal showed that it was a C-form crystal.

Example 6

The ethanolate of the compound (A) (0.40 g) was suspended in 10 mL of isopropyl ether/methanol (9/1), and the suspension was stirred for 3 days at 25° C. Further, 50 mL of isopropyl ether/methanol (9/1) was added, and the system was suspended for 6 days at 25° C. After centrifugation (3000 rpm, 25° C., 10 minutes), the supernatant was removed, and the residue was dried at room temperature to obtain a colorless crystal. The X-ray powder diffraction pattern and differential thermal analysis/thermogravimetric analysis (TG/DTA) of the resulting crystal showed that it was a crystal of a dihydrate.

Test Example 1

(1) Creation of CHO-K1 cells stably expressing human SGLT1

A plasmid vector expressing human SGLT1 protein was transfected into CHO-K1 cells using lipofectamine 2000 (Invitrogen). The cells were cultured in the presence of 500 µg/mL geneticin to select resistant strains, followed by screening in the system shown below using sugar uptake capacity as an indicator to obtain SGLT1-expressing cells.

(2) Creation of CHO-K1 cells stably expressing human SGLT2

Method A (described in WO2007/136116): A plasmid vector expressing human SGLT2 protein modified to have Leu-GluSerArgGlyProVal added to the carboxy-terminal final residue was transfected into CHO-K1 cells using lipofectamine 2000 (Invitrogen). The cells were cultured in the presence of 500 µg/mL hygromycin B to select resistant strains, followed by screening in the system shown below using sugar uptake capacity as an indicator to obtain SGLT2-expressing cells. The results calculated by using these stably expressing cells are shown in Table 1 as Method A.

Method B: A plasmid vector expressing human SGLT2 protein was transfected into CHO-K1 cells using lipofectamine LTX (Invitrogen). The cells were cultured in the presence of 1000 µg/mL geneticin to select resistant strains, followed by screening in the system shown below using sugar uptake capacity as an indicator to obtain SGLT2-expressing cells. The results calculated by using these stably expressing cells are shown in Table 1 as Method B.

(3) Inhibition test for sodium-dependent sugar uptake in stably expressing cells The stably expressing cells prepared above were used in the following test.

Pretreatment buffer (140 mM choline chloride, 2 mM KCl, 1 mM $CaCl_2$, 1 mM $MgCl_2$, 10 mM HEPES/5 mM Tris, pH 7.4) was added in a volume of 200 μL to the cells stably expressing SGLT1 or 2 mL for Method A and 200 μL for Method B to the cells stably expressing SGLT2, followed by incubation for 20 minutes. The pretreatment buffer was removed and replaced by uptake buffer containing a test compound (1 mM methyl α-D-glucopyranoside (containing [$^{14}$C]methyl α-D-glucopyranoside), 140 mM NaCl, 2 mM KCl, 1 mM $CaCl_2$, 1 mM $MgCl_2$, 10 mM HEPES/5 mM Tris, pH 7.4) in a volume of 75 μL for SGLT1 and SGLT2 in Method B or 200 μL for SGLT2 in Method A. Uptake reaction was performed at 37° C. for 30 minutes (SGLT1) or 60 minutes (SGLT2). After the reaction, the cells were washed twice with washing buffer (10 mM methyl α-D-glucopyranoside, 140 mM choline chloride, 2 mM KCl, 1 mM $CaCl_2$, 1 mM $MgCl_2$, 10 mM HEPES/5 mM Tris, pH 7.4) in a volume of 200 μL for SGLT1 and SGLT2 in Method B or 2 mL for SGLT2 in Method A, and then dissolved in a 0.25 M NaOH solution (75 μL for SGLT1 and SGLT2 in Method B or 400 μL for SGLT2 in Method A). A liquid scintillator (Perkin Elmer) was added and mixed well with each sample, followed by measurement of radioactivity using a β-ray analyzer. For the control group, uptake buffer containing no test compound was prepared. Moreover, another uptake buffer containing choline chloride instead of NaCl was also prepared for basal uptake.

For determination of $IC_{50}$ values, test compounds prepared at 6 appropriate concentrations were used and their concentrations required for 50% inhibition of the amount of sugar uptake ($IC_{50}$ values) were calculated relative to the amount of sugar uptake in the control group (100%). The test results obtained are shown in Table 1.

TABLE 1

| Compound | $IC_{50}$ for hSGLT1 (nM) | $IC_{50}$ for hSGLT2 (nM) Method A | $IC_{50}$ for hSGLT2 (nM) Method B |
|---|---|---|---|
| (A) | 29 | 1276 | 20 |

Table 1 shows that the compound (A) exhibits strong SGLT1 inhibiting activity and also exhibits some, although weak, SGLT2 inhibiting activity.

The superiority of the compound (A) over compounds of similar structures will be shown below.

Test Example 2

Confirmation study of hypoglycemic effect in streptozotocin diabetic model rats (1) Preparation of Diabetic Model Rats SD/IGS rats at 7 weeks of age (male, Charles River Laboratories Japan Inc.) were fasted for about 16 hours and then injected with 50 mg/kg streptozotocin (STZ) via the caudal vein under ether anesthesia to prepare diabetic model rats. Similarly, another group of SD/IGS rats at 7 weeks of age was injected with 1.25 mmol/L citric acid in physiological saline (1 mL/kg) via the tail vein under ether anesthesia to prepare normal control rats. At one week after injection of STZ or 1.25 mmol/L citric acid in physiological saline, the rats (8 weeks old) were provided for an oral glucose tolerance test.

(2) Oral Glucose Tolerance Test

After the diabetic model rats were fasted for about 16 hours, drug groups were each orally administered with a drug (1 mg/kg) dissolved in a 0.5% carboxymethylcellulose sodium (CMC) aqueous solution, while the control group was orally administered with a 0.5% aqueous CMC solution alone. At 5 minutes after drug administration, a glucose solution (2 g/kg) was orally administered to each rat, and the blood was collected at a total of 5 time points: before drug administration (0 time), and at 0.25, 0.5, 1 and 2 hours after the oral administration.

Blood was collected from the caudal veins of the rats under ether anesthesia with the use of a heparin-coated blood collecting tube and centrifuged, whereafter blood plasma was separated. Plasma glucose concentrations were quantified by measurement with a Glucose CII-Test Wako (Wako Pure Chemical Industries, Ltd., Japan). To determine the intensity of hypoglycemic effect, the blood glucose level before drug administration was subtracted from each blood glucose level measured until one hour after oral administration in each drug group, and the resulting values were analyzed by the trapezoidal method to calculate an increment in the area under the curve for glucose (ΔAUC), which was expressed as a decrease relative to ΔAUC of the control group.

The results obtained are shown in Table 2 and Table 3.

Test Example 3

(1) Changes in Renal Concentrations of Compounds Disclosed in WO2007/136116 Until One Week after Oral Administration SD/IGS rats at 7 weeks of age (male, non-fasting, Charles River Laboratories Japan Inc.) were orally administered with compound 4, 10 or 33 (1 mg/kg each) or compound 11 (0.3 mg/kg) prepared in a 0.5% aqueous CMC solution. At 24, 72 and 168 hours after drug administration, the rats were exsanguinated via the postcaval vein under ether anesthesia, and their kidneys were excised after they were confirmed to be euthanized. After the tissue surface was washed with physiological saline, each tissue was measured for its weight and homogenized in 4 volumes of purified water under ice cooling. To each homogenate, an acetonitrile/methanol solution containing an internal standard substance was added to remove proteins, and the supernatant was then subjected to LC-MS/MS (Applied Biosystems API3000). Drug-derived ions generated by electrospray ionization in positive ion mode were detected by selective reaction monitoring. The peak area of the resulting extracted ion chromatogram was analyzed by the internal standard method to calculate the drug concentration in the homogenate.

As the internal standard material for Compounds 10 and 33, (1S)-1,5-anhydro-1-[5-(4-ethoxybenzyl)-2-methoxy-4-methylphenyl]-1-thio-D-glucitol,ethyl-$D_5$ was used. As the internal standard materials for Compounds 4 and 11, Compound II and deuterium-labeled Compound II (trishydroxymethyl-$D_6$; —$C(CD_2OH)_3$), respectively, were used.

The experimental results obtained are shown in Table 2.

(2) Renal Concentrations of the Compound (A) of the Present Invention after Repeated Oral Administration for 3 Days SD/IGS rats at 7 weeks of age (male, non-fasting, Charles River Laboratories Japan Inc.) were orally administered once a day for 3 consecutive days with the compound (A) (3 mg/kg) prepared in a 0.5% aqueous CMC solution. At 48 hours after the final drug administration, the rats were exsanguinated via the postcaval vein under isoflurane anesthesia, and their kidneys were excised after they were confirmed to be euthanized. After the tissue surface was washed with physiological saline, each tissue was measured for its weight and homogenized in 4 volumes of purified water under ice cooling. The drug concentration in each homogenate was determined in the same manner as shown in Test Example 3(1) by LC-MS/MS using compound II as an internal standard substance.

The experimental results are shown in Table 3.

TABLE 2

Glucose tolerance test results and renal concentrations of prior art compounds

| compound No. in | STZ rats OGTT$ % inhibition $\Delta AUC_{0-1\,h}$ | Concentration of compounds in kidney after single oral administration at a dose of 1 mg/kg to male Sprague-Dawley rats. | | |
|---|---|---|---|---|
| WO2007/ 136116 | (mg/dl) @1 mg/kg/po | After 1 day (ng/g) | After 3 days (ng/g) | After 7 days (ng/g) |
| compound 4 | 51 | 68.4 ± 7.49 | 85.5 ± 23.1 | 76.3 ± 15.5 |
| compound 10 | 69 | 167 ± 36.3 | 124 ± 12.2 | 53.8 ± 7.6 |

TABLE 2-continued

Glucose tolerance test results and renal concentrations of prior art compounds

| compound No. in | STZ rats OGTT$ % inhibition $\Delta AUC_{0-1\,h}$ | Concentration of compounds in kidney after single oral administration at a dose of 1 mg/kg to male Sprague-Dawley rats. | | |
|---|---|---|---|---|
| WO2007/ 136116 | (mg/dl) @1 mg/kg/po | After 1 day (ng/g) | After 3 days (ng/g) | After 7 days (ng/g) |
| compound 11 | 68 | 63.5 ± 20.1* | 67.3 ± 3.15* | 48.7 ± 18.3* |
| compound 33 | 81# | 29.8 ± 6.79 | 25.5 ± 8.68 | 16.2 ± 3.11 |

*The value represents mean ± S.D. when compound 11 was orally administered at 0.3 mg/kg.
$Suppression of glucose $AUC_{0-1\,h}$ in streptozotocin (STZ)-induced diabetic rats versus vehicle control, following an oral dose at 1 mg/kg.
OGTT using Sprague-Dawley rats.

The structures of compounds 4, 10, 11 and 33 disclosed in WO2007/136116 are shown below.

[Formula 17]

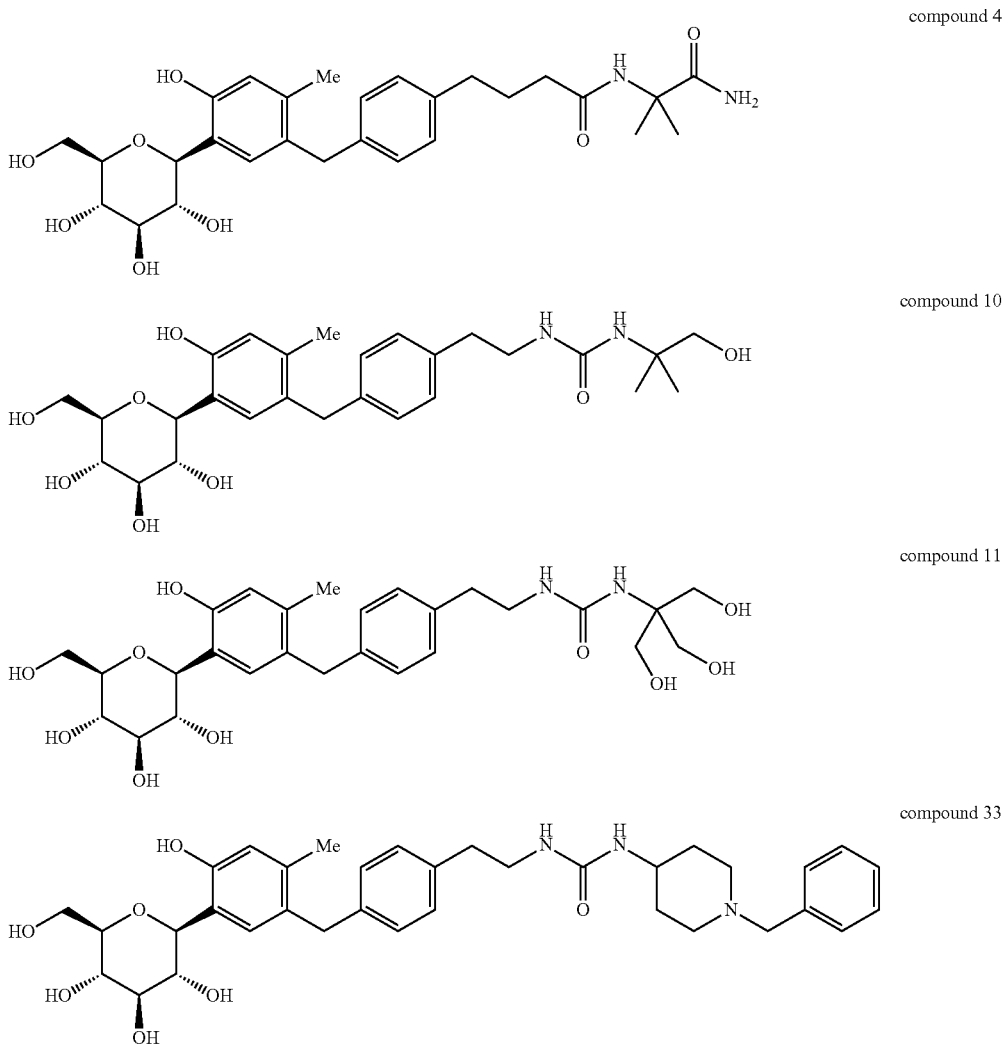

compound 4 compound 10 compound 11 compound 33

TABLE 3

| compound | STZ rats OGTT* % inhibition $\Delta AUC_{0-1\,h}$ (mg/dl) @1 mg/kg/po | Concentration of compounds in kidney after 3 days continuous oral administration at a dose of 3 mg/kg to male Sprague-Dawley rats. After 2 days (ng/g) |
|---|---|---|
| (A) | 65 | ND |

*Suppression of glucose $AUC_{0-1\,h}$ in STZ-induced diabetic rats versus vehicle control, following an oral dose at 1 mg/kg.
ND (not determined) means limit of detection (5 ng/g).

The compounds disclosed in WO2007/136116 exhibited potent hypoglycemic action in the glucose tolerance test after oral administration of 1 mg/kg. Following the oral administration of 1 mg/kg, however, the elimination rates of the compounds from within the kidney were so slow that the compounds tended not to be excreted, but to remain in the kidney, even after 7 days (Table 2).

On the other hand, the compound (A) had potent hypoglycemic action, like the above-mentioned prior art compounds. Moreover, this compound exhibited a characteristic feature in that even when it was administered in a dose of 3 mg/kg for 3 consecutive days, it unexpectedly did not remain in the kidney at subsequent day 2 (Table 3).

A possible cause of this difference is that the compound (A) has been rapidly excreted, without remaining in the kidney, when absorbed in the body.

Thus, the compounds of the present invention have no tendency to remain in the body and are less likely to cause side effects and toxicity due to continuous administration, and hence appear to have practically excellent properties as pharmaceutical preparations.

INDUSTRIAL APPLICABILITY

The crystal of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol according to the present invention has excellent storage stability and other physical properties. It is useful as a drug substance, and suitable for industrial production.

The invention claimed is:

1. A crystal of an ethanolate of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol having physical properties (a) to (c) mentioned below:
(a) Having peaks at 2θ=5.9 degrees, 17.1 degrees, 17.6 degrees and 21.5 degrees in X-ray powder diffraction (Cu—Kα);
(b) Showing characteristic absorption bands at 3538 cm$^{-1}$, 3357 cm$^{-1}$, 2964 cm$^{-1}$, 1673 cm$^{-1}$, 1634 cm$^{-1}$ and 1505 cm$^{-1}$ in an infrared absorption spectrum; and
(c) Having a melting point in a vicinity of 111° C.

2. A process for producing a crystal having physical properties (a) to (c) mentioned below, comprising:
dissolving (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol in ethanol or a mixture of ethanol and an organic solvent miscible with ethanol;
then effecting crystallization at 0 to 80° C.; and
drying the resulting crystal at 50° C. or lower.
(a) Having peaks at 2θ=5.9 degrees, 17.1 degrees, 17.6 degrees and 21.5 degrees in X-ray powder diffraction (Cu—Kα);
(b) Showing characteristic absorption bands at 3538 cm$^{-1}$, 3357 cm$^{-1}$, 2964 cm$^{-1}$, 1673 cm$^{-1}$, 1634 cm$^{-1}$ and 1505 cm$^{-1}$ in an infrared absorption spectrum; and
(c) Having a melting point in a vicinity of 111° C.

3. A crystal of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol having physical properties (a) to (b) mentioned below:
(a) Having peaks at 2θ=6.1 degrees, 13.7 degrees, 18.0 degrees and 18.7 degrees in X-ray powder diffraction (Cu—Kα); and
(b) Having a melting point in a vicinity of 110° C.

4. A process for producing a crystal having physical properties (a) to (b) mentioned below, comprising:
suspending an ethanolate of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol in water or a phosphate buffer solution; and
then drying the resulting crystal at 35° C. or lower.
(a) Having peaks at 2θ=6.1 degrees, 13.7 degrees, 18.0 degrees and 18.7 degrees in X-ray powder diffraction (Cu—Kα); and
(b) Having a melting point in a vicinity of 110° C.

5. A crystal of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol having physical properties (a) to (b) mentioned below:
(a) Having peaks at 2θ=6.4 degrees, 10.9 degrees, 16.9 degrees and 18.1 degrees in X-ray powder diffraction (Cu—Kα); and
(b) Having a melting point in a vicinity of 115° C.

6. A process for producing a crystal having physical properties (a) to (b) mentioned below, comprising:
suspending an ethanolate of (1S)-1,5-anhydro-1-[5-(4-{(1E)-4-[(1-{[2-(dimethylamino)ethyl]amino}-2-methyl-1-oxopropan-2-yl)amino]-3,3-dimethyl-4-oxobut-1-en-1-yl}benzyl)-2-methoxy-4-(propan-2-yl)phenyl]-D-glucitol in a mixture of isopropyl ether and an organic solvent (excluding ethanol) miscible with isopropyl ether, or a mixture of hexane or heptane and an organic solvent (excluding ethanol) miscible with hexane or heptane; and
then drying the resulting crystal at room temperature to 100° C.:
(a) Having peaks at 2θ=6.4 degrees, 10.9 degrees, 16.9 degrees and 18.1 degrees in X-ray powder diffraction (Cu—Kα); and
(b) Having a melting point in a vicinity of 115° C.

* * * * *